United States Patent
Song

(10) Patent No.: US 10,632,106 B2
(45) Date of Patent: *Apr. 28, 2020

(54) METHODS OF CANCER TREATMENT WITH 2-(1'H-INDOLE-3'-CARBONYL)-THIAZOLE-4-CARBOXYLIC ACID METHYL ESTER

(71) Applicant: Ariagen, Inc., Menlo Park, CA (US)

(72) Inventor: Jiasheng Song, Madison, WI (US)

(73) Assignee: Ariagen, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/047,805

(22) Filed: Jul. 27, 2018

(65) Prior Publication Data

US 2019/0134009 A1 May 9, 2019

Related U.S. Application Data

(60) Continuation-in-part of application No. 15/613,808, filed on Jun. 5, 2017, now Pat. No. 10,195,182, which is a continuation of application No. 14/961,325, filed on Dec. 7, 2015, now Pat. No. 9,694,000, which is a continuation of application No. 13/952,030, filed on Jul. 26, 2013, now Pat. No. 9,238,645, which is a division of application No. 13/503,657, filed as application No. PCT/US2010/052729 on Oct. 14, 2010, now Pat. No. 8,604,067, application No. 16/047,805, which is a continuation of application No. 13/954,834, filed on Jul. 3, 2013, now abandoned, which is a continuation-in-part of application No. 13/503,657, filed as application No. PCT/US2010/052729 on Oct. 14, 2010, now Pat. No. 8,604,067.

(60) Provisional application No. 61/257,422, filed on Nov. 2, 2009.

(51) Int. Cl.

| | | |
|---|---|---|
| A61K 31/427 | (2006.01) | |
| A61P 35/00 | (2006.01) | |
| C07D 417/06 | (2006.01) | |
| A61K 31/475 | (2006.01) | |
| A61K 31/40 | (2006.01) | |
| A61K 31/425 | (2006.01) | |
| A61K 45/06 | (2006.01) | |

(52) U.S. Cl.
CPC ........... *A61K 31/427* (2013.01); *A61K 31/40* (2013.01); *A61K 31/425* (2013.01); *A61K 31/475* (2013.01); *A61K 45/06* (2013.01); *C07D 417/06* (2013.01)

(58) Field of Classification Search
USPC ........................................................ 514/365
See application file for complete search history.

(56) References Cited

U.S. PATENT DOCUMENTS

| | | |
|---|---|---|
| 6,916,834 B2 | 7/2005 | DeLuca et al. |
| 7,002,019 B2 | 2/2006 | DeLuca et al. |
| 7,419,992 B2 | 9/2008 | DeLuca et al. |
| 2002/0177594 A1 | 11/2002 | Curtin et al. |
| 2002/0183524 A1 | 12/2002 | DeLuca et al. |
| 2012/0214853 A1 | 8/2012 | Song |
| 2013/0338201 A1 | 12/2013 | Song |

FOREIGN PATENT DOCUMENTS

| | | |
|---|---|---|
| EP | 1842541 A1 | 10/2007 |
| WO | WO 1998/039330 | 9/1998 |
| WO | WO 2002/028832 | 4/2002 |
| WO | WO 2002/064138 | 8/2002 |
| WO | WO 2003/068742 | 8/2003 |
| WO | WO 2004/060888 | 7/2004 |
| WO | WO 2006/029862 | 3/2006 |
| WO | WO 2009/067349 | 5/2009 |
| WO | WO 2009/070645 | 6/2009 |
| WO | WO 2013/033003 | 3/2013 |
| WO | WO 2013/041468 | 3/2013 |

OTHER PUBLICATIONS

Akahoshi et al., "Synthesis, structure-activity relationships, and pharmacokinetic profiles of nonpeptidic α-Keto Heterocycles as novel inhibitors of human chymase," J. Med. Chem. 44:1286-1296 (2001).
Bankoti et al., "Functional and phenotypic effects of AhR activation in inflammatory dendritic cells," Toxicol Appl Pharmacol 246:18-28 (2010).
Bermúdez et al., "Beta-naphthoflavone represses dystrophin Dp71 expression in hepatic cells," Biochim. Biophys. Acta. 1759(3-4):152-158 (2006).
Bock et al., "Ah receptor- and TCDD-mediated liver tumor promotion: clonal selection and expansion of cells evading growth arrest and apoptosis," Biochem. Pharmacol. 69(10):1403-1408 (2005).
Brauze et al., "The effect of aryl hydrocarbon receptor ligands on the expression of AhR, AhRR, ARNT, Hif1alpha, CYP1A1 and NQO1 genes in rat liver," Toxicol. Lett. 167(3):212-220 (2006).
Cook et al., "Angiogenesis Inhibitors: Current Strategies and Future Prospects," http://cajournal.org (2010).
Dietrich et al., "The aryl hydrocarbon receptor (AhR) in the regulation of cell-cell contact and tumor growth," Carcinogenesis 31(8):1319-1328 (2010).
Ebos et al., "Accelerated metastasis after short-term treatment with a potent inhibitor of tumor angiogenesis," Cancer Cell 15(3):232-239 (2009).
Elizondo et al., "Altered cell cycle control at the G(2)/M phases in aryl hydrocarbon receptor-null embryo fibroblast," Mol Pharmacol 57(5):1056-63 (2000).

(Continued)

*Primary Examiner* — Kathrien A Cruz
(74) *Attorney, Agent, or Firm* — Steptoe & Johnson LLP; Z. Ying Li

(57) ABSTRACT

Provided herein are methods of cancer treatment by administering an effective amount of an endogenous ligand for the aryl hydrocarbon (Ah) receptor (AhR) named ITE or one of its structural analogs to a patient with cancer, for example, prostate, liver, lung, ovarian, breast, skin, colon (or rectum), stomach, pancreatic, kidney, bladder, soft tissue, or cervical cancer.

10 Claims, 5 Drawing Sheets

(56) References Cited

OTHER PUBLICATIONS

Ellis, "Role of Angiogenesis Inhibitors in Cancer Treatment," Oncology 15:39-46 (2001).
English et al., "VEGF inhibition and metastasis: possible implications for anti angiogenic therapy," Cancer Biol. Ther. 8(13):1214-1225 (2009).
Fritz et al., "The selective aryl hydrocarbon receptor modulator 6-methyl-1,3,8-trichlorodibenzofuran inhibits prostate tumor metastasis in TRAMP mice," Biochem. Pharmacol. 77(7):1151-1160 (2009).
Fuganti et al., "A general method for the synthesis of the most powerful naturally occurring Maillard flavors," Tetrahedron 63:4762-4767 (2007).
Gierthy et al., "Correlation of in vitro and in vivo growth suppression of MCF-7 human breast cancer by 2,3,7,8-tetrachlorodibenzo-p-dioxin," Cancer Res 53(13):3149-3153 (1993).
Gluschnaider et al., "beta-TrCP inhibition reduces prostate cancer cell growth via upregulation of the aryl hydrocarbon receptor," PLoS One 5(2):e9060 (2010).
Hall et al., "Activation of the Aryl-Hydrocarbon Receptor Inhibits Invasive and Metastatic Features of Human Breast Cancer Cells and Promotes Breast Cancer Cell Differentiation," Mol Endocrinol 24:359-369 (2010).
Henry et al., "A potential endogenous ligand for the aryl hydrocarbon receptor has potent agonist activity in vitro and in vivo," Arch. Biochem. Biophys. 450(1):67-77 (2006).
Henry et al., "TCDD and a Putative Endogenous AhR Ligand, ITE, Elicit the Same Immediate Changes in Gene Expression in Mouse Lung Fibroblasts," Toxicological Sciences 114:90-100 (2010).
Heravi et al., "An efficient synthesis of thiazol-2-imine derivatives via a onepot, three-component reaction," Tetrahedron Letters 53:392-394 (2012).
Holcomb et al., "Inhibition of 7,12-dimethylbenzanthracene-induced rat mammary tumor growth by 2,3,7,8-tetrachlorodibenzo-p-dioxin," Cancer Lett 82(1):43-7 (1994).
Ishida et al., "Activation of the aryl hydrocarbon receptor pathway enhances cancer cell invasion by upregulating the MMP expression and is associated with poor prognosis in upper urinary tract urothelial cancer," Carcinogenesis 31(2):287-295 (2010).
Jana et al., "Cross-talk between 2,3,7,8-tetrachlorodibenzo-p-dioxin and testosterone signal transduction pathways in LNCaP prostate cancer cells," Biochem Biophys Res Commun 256(3):462-8 (1999).
John et al., "Antiangiogenic therapy and surgical practice," Br J Surg 95(3):281-293 (2008).
Johnson, et al., "Total synthesis of (−)-Rhazinilam: asymmetric C—H bond activation via the use of chiral auxiliary," J. Am. Chem. Soc. 124:6900-6903 (2002).
Jux et al., "Langerhans cell maturation and contact hypersensitivity are impaired in aryl hydrocarbon receptor-null mice," J. Immunol. 182(11):6709-6717 (2009).
Kajta et al., "Aryl hydrocarbon receptor-mediated apoptosis of neuronal cells: a possible interaction with estrogen receptor signaling," Neuroscience 158(2):811-822 (2009).
Kashani et al., "Expression of the aryl hydrocarbon receptor (AhR) and the aryl hydrocarbon receptor nuclear translocator (ARNT) in fetal, benign hyperplastic, and malignant prostate," Prostate 37(2):98-108 (1998).
Kawajiri, et al., "Aryl hydrocarbon receptor suppresses intestinal carcinogenesis in ApcMin/+ mice with natural ligands," Proc. Natl. Acad. Sci. U.S.A. 106(32):13481-13486 (2009).
Kerbel, "Tumor angiogenesis: past, present and the near future," Carcinogenesis 21:505-515 (2000).
Knerr et al., "Carcinogenicity of 2,3,7,8-tetrachlorodibenzo-p-dioxin in experimental models," Mol Nutr Food Res 50(10):897-907 (2006).
Koliopanos et al., "Increased aryl hydrocarbon receptor expression offers a potential therapeutic target for pancreatic cancer," Oncogene 21(39):6059-70 (2002).
Lin et al., "Overexpression of aryl hydrocarbon receptor in human lung carcinomas," Toxicol Pathol 31(1):22-30 (2003).
Liu et al., "AhR expression is increased in hepatocellular carcinoma," J Mol Histol 44(4):455-61 (2013).
Loges et al., "Silencing or fueling metastasis with VEGF inhibitors: antiangiogenesis revisited," Cancer Cell 15(3):167-170 (2009).
Marlowe et al., "The aryl hydrocarbon receptor displaces p300 from E2F-dependent promoters and represses S phase-specific gene expression," J Biol Chem 279(28):29013-22 (2004).
McDougal et al., "Tamoxifen-induced antitumorigenic/antiestrogenic action synergized by a selective aryl hydrocarbon receptor modulator," Cancer Res 61(10):3902-3907 (2001).
McDougal et al., "Inhibition of 7,12-dimethylbenz [a] anthracene-induced rat mammary tumor growth by aryl hydrocarbon receptor agonists," Cancer Lett 120(1):53-63 (1997).
Milinkevich et al., "Synthesis of 5-(Thiazol-5-yl)-4,5-dihydroisoxazoles from 3-Chloropentane-2,4-dione," J. Comb. Chem. 10:521-525 (2008).
Mizzoni et al., "Some thiazolines and thiazolidinones with antituberculous activity," (Jul. 5, 1958).
Mjambili et al., "Synthesis and biological evaluation of 2-aminothiazole derivatives as antimycobacterial and antiplasmodial agents," Biorganic & Medicinal Chemistry Letters 24:560-564 (2014).
Morrow et al., "Aryl hydrocarbon receptor-mediated inhibition of LNCaP prostate cancer cell growth and hormone-induced transactivation," J. Steroid Biochem. Mol. Biol. 88(1):27-36 (2004).
Narender et al., "Aqueous phase synthesis of thiazoles and aminothiazoles in the presence of β-cyclodextrin," Tetrahedron letters 46:5953-5955 (2005).
O'Donnell et al., "The aryl hydrocarbon receptor mediates leflunomide-induced growth inhibition of melanoma cells," PLoS One 7(7) (2012).
Oenga et al., "TCDD and PCBs inhibit breast cancer cell proliferation in vitro," Toxicol in Vitro. 18(6):811-9 (2004).
Okino et al., "Toxic and chemopreventive ligands preferentially activate distinct aryl hydrocarbon receptor pathways: implications for cancer prevention," Cancer Prey Res (Phila Pa). 2(3):251-256 (2009).
Ozawa et al., "A new synthesis of glutathione via the thiazoline peptide," Bull. Chem. Soc. Jpn., 53:2592-2593 (1980).
Paez-Ribes et al., "Antiangiogenic therapy elicits malignant progression of tumors to increased local invasion and distant metastasis," Cancer Cell 15(3):220-231 (2009).
Park et al., "The aryl hydrocarbon receptor predisposes hepatocytes to Fas mediated apoptosis," Mol Pharmacol. 67(3):612-22 (2005).
Patani et al., "Bioisosterism: A Rational Approach to Design," Chemical Reviews 96(8):3147-3176 (1996).
Peng et al., "Potential therapeutic significance of increased expression of aryl hydrocarbon receptor in human gastric cancer," World J. Gastroenterol. 15(14):1719-1729 (2009).
Piparo et al., "Virtual screening for aryl hydrocarbon receptor binding prediction," J Med Chem 49(19):5702-5709 (2006).
Poland et al., "2,3,7,8-tetrachlorodibenzo-p-dioxin and related halogenated aromatic hydrocarbons: examination of the mechanism of toxicity," Annu. Rev. Pharmacol. Toxicol. 22:517-554 (1982).
Poellinger, "Mechanistic aspects—the dioxin (aryl hydrocarbon) receptor," Food Addit Contam 17(4):261-6 (2000).
Puga et al., "Ah receptor signals cross-talk with multiple developmental pathways," Biochem Pharmacol. 69(2)199-207 (2005).
Puga et al., "Role of the aryl hydrocarbon receptor in cell cycle regulation," Toxicology 181-182:171-7 (2002).
Quintana et al., "Control of T(reg) and T(H)17 cell differentiation by the aryl hydrocarbon receptor," Nature 453(7191):65-71 (2008).
Quintana et al., "An endogenous aryl hydrocarbon receptor ligand acts on dendritic cells and T cells to suppress experimental autoimmune encephalomyelitis," Proc Natl Acad Sci U S A 107:20768-73 (2010).
Ray et al., "Activation of the aryl hydrocarbon receptor by TCDD inhibits senescence: a tumor promoting event?" Biochem. Pharmacol 77(4):681-688 (2009).
Rose, "A theory of the action of cancer chemotherapeutic drugs," Clin. Exp. Immunol. 2:361-373 (1967).

(56) References Cited

OTHER PUBLICATIONS

Roukos et al., "Current concerns and challenges regarding tailored antiangiogenic therapy in cancer," Expert Rev Anticancer Ther. 9(10):1413-1416 (2009).
Safe et al., "Mechanism of action and development of selective aryl hydrocarbon receptor modulators for treatment of hormone dependent cancers," Int J Oncol 20(6):1123-1128 (2002).
Sanderson et al., "2,3,7,8-Tetrachlorodibenzo-p-dioxin and diindolylmethanes differentially induce cytochrome P450 1A1, 1B1, and 19 in H295R human adrenocortical carcinoma cells," Toxicol. Sci. 61(1):40-48 (2001).
Shih et al., "Bevacizumab: an angiogenesis inhibitor for the treatment of solid malignancies," Clin Ther (11): 1779-802 (2006).
Simon et al., "Estimates of cancer potency of 2,3,7,8-tetrachlorixlibenzo(p)dioxin using linear and nonlinear dose-response modeling and toxicokinetics," Toxicological sciences 112(2):490-506 (2009).
Singh et al. "Primary peripheral T cells become susceptible to 2,3,7,8-tetrachlorodibenzo-p-dioxin-mediated apoptosis in vitro upon activation and in the presence of dendritic cells," Mol. Pharmacol. 73(6):1722-1735 (2008).
Solankee, et al., "Thiazoline: synthesis and antitubercular activity of 2-Alkyl/Aryl/-5-(w-carboxy pentyl) thiazolin-4-one," Part II, J. Inst. Chemists (India) vol. 66 (1994).
Song et al., "A ligand for the aryl hydrocarbon receptor isolated from lung," Proc Natl Acad Sci USA. 99(23):14694-9 (2002).
Stevens et al., "The aryl hydrocarbon receptor: a perspective on potential roles in the immune system," Immunology 127(3):299-311 (2009).
Sutter et al., "EGF receptor signaling blocks aryl hydrocarbon receptor mediated transcription and cell differentiation in human epidermal keratinocytes," Proc. Natl. Acad. Sci. U.S.A. 106(11):4266-4271 (2009).
Yu et al., "In utero exposure of mice to dibenzo[a,l] pyrene produces lymphoma in the offspring: role of the aryl hydrocarbon receptor," Cancer Res 66(2):755-762 (2006).
Van Zandt et al., "Discovery of 3-[(4,5,7-Trifluorobenzothiazol-2-yl)methyl]indole-N-acetic acid (lidorestat) and congeners as highly potent and selective inhibitors of aldose reductase for treatment of chronic diabetic complications," J. Med. Chem. 48:3141-3152 (2005).
Veldhoen et al., "The aryl hydrocarbon receptor links TH17-cell-mediated autoimmunity to environmental toxins," Nature 453(7191):106-109 (2008).
Wang, et al., "An endogenous aryl hydrocarbon receptor ligand inhibits proliferation and migration of human ovarian cancer cells," Cancer Letters 340:63-71 (2013).
Zhang et al., "The aryl hydrocarbon receptor as a target for estrogen receptor-negative breast cancer chemotherapy," Endocr Relat Cancer 16(3):835-844 (2009).
Zhang et al., "Activation of aryl hydrocarbon receptor suppresses invasion of esophageal squamous cell carcinoma cell lines," Tumori 98(1):152-157 (2012).
"Fruit juice and medications don't mix," Consumer Reports News (Sep. 2, 2008).
USPTO, PTAB decision on the appeal of U.S. Appl. No. 13/954,834, 17 pages (dated May 30, 2018).
Classic Bioelectronic isosteres.

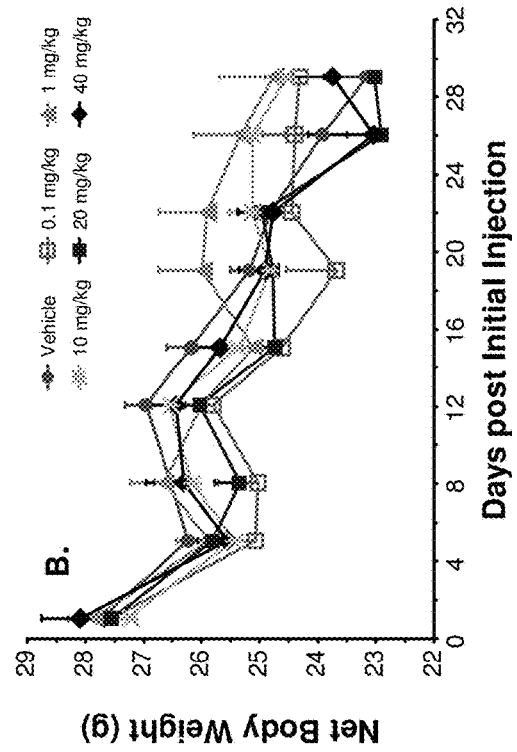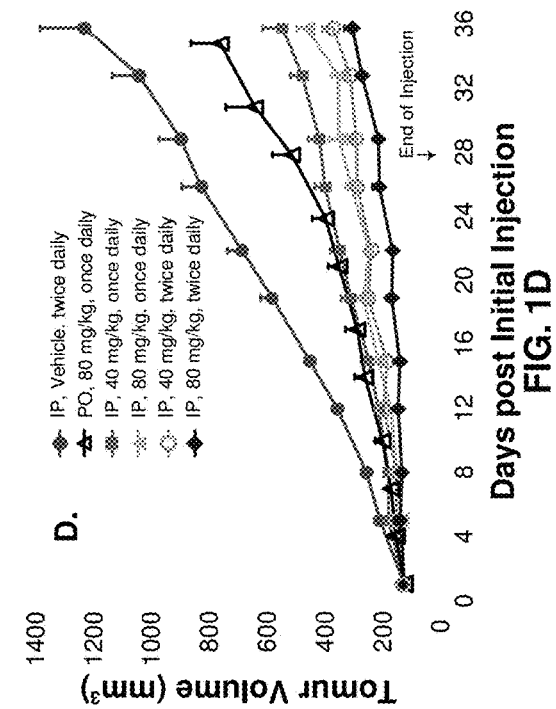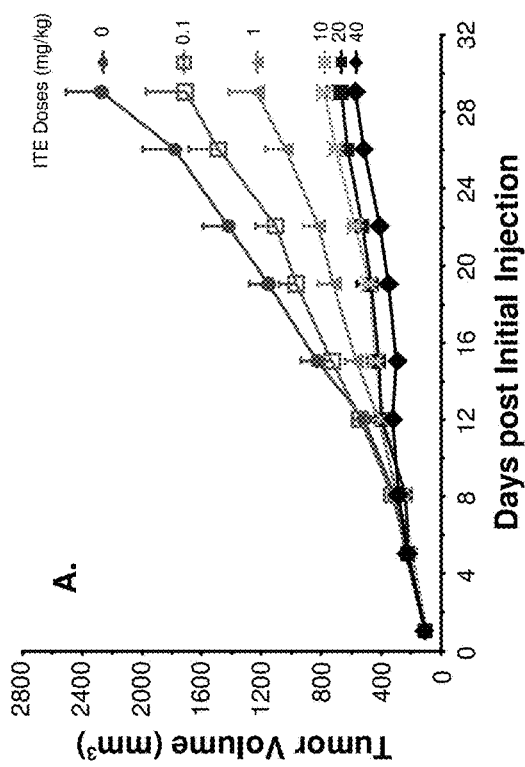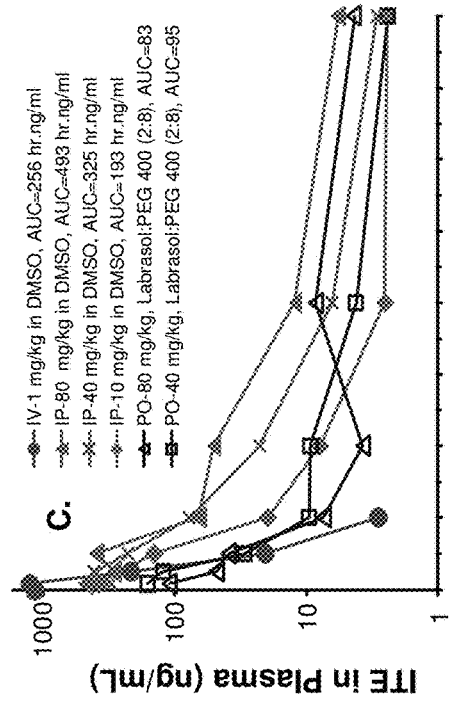
FIG. 1A
FIG. 1B
FIG. 1C
FIG. 1D

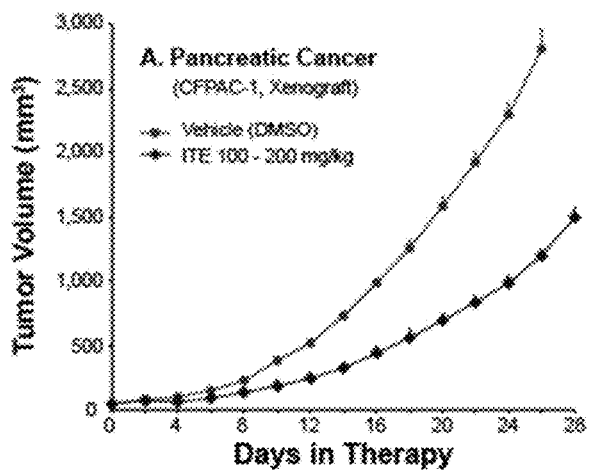
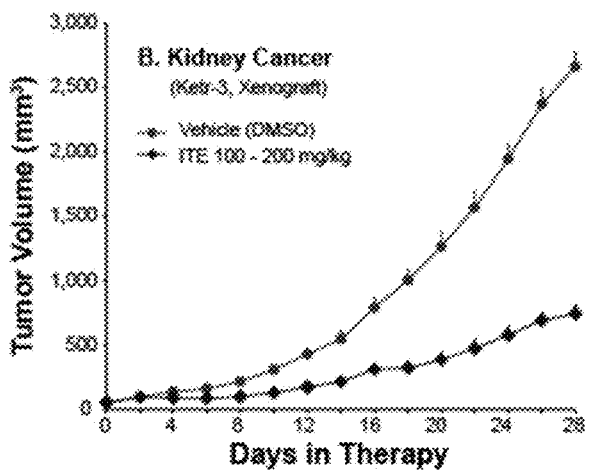
FIG. 5A
FIG. 5B
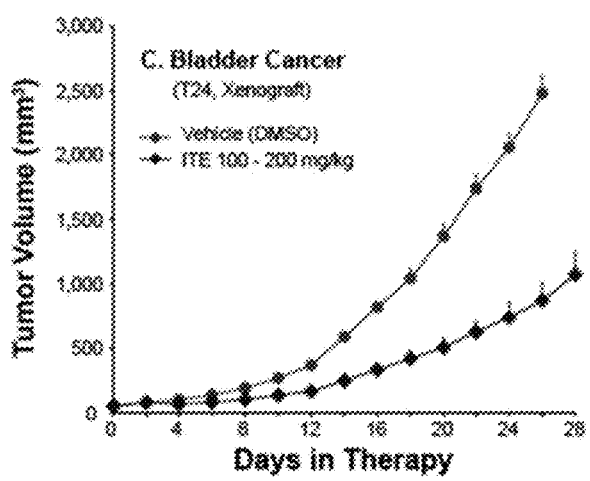
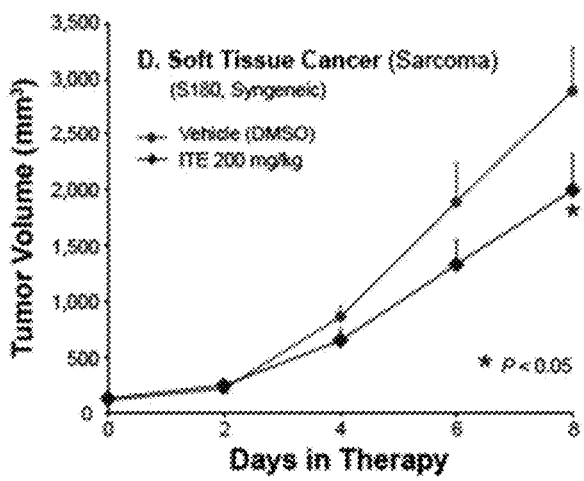
FIG. 5C
FIG. 5D
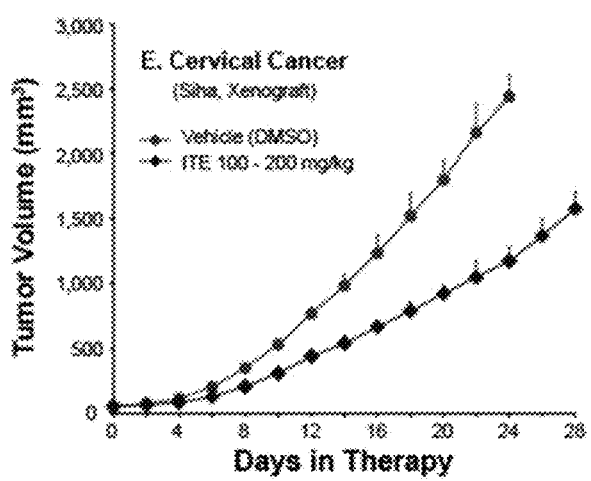
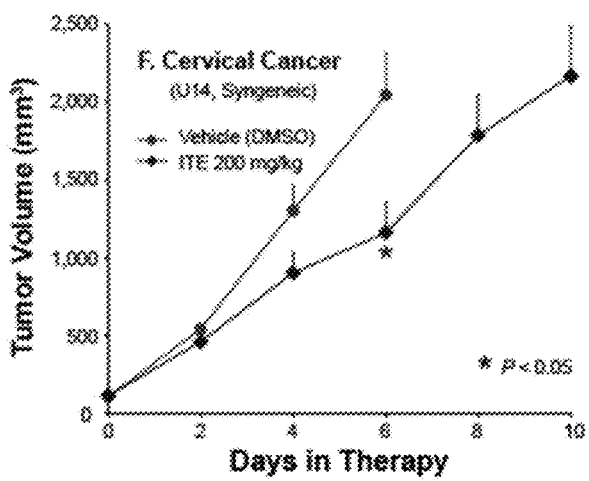
FIG. 5E
FIG. 5F

METHODS OF CANCER TREATMENT WITH 2-(1'H-INDOLE-3'-CARBONYL)-THIAZOLE-4-CARBOXYLIC ACID METHYL ESTER

RELATED APPLICATIONS

This application is a continuation-in-part of U.S. application Ser. No. 15/613,808, filed Jun. 5, 2017, which is a continuation of U.S. application Ser. No. 14/961,325, filed Dec. 7, 2015, now U.S. Pat. No. 9,694,000, which is a continuation of Ser. No. 13/952,030, filed Jul. 26, 2013, now U.S. Pat. No. 9,238,645, which is a division of U.S. application Ser. No. 13/503,657, filed Apr. 24, 2012, now U.S. Pat. No. 8,604,067, which is a national stage application of PCT/US2010/052729, filed Oct. 14, 2010, which claims priority from U.S. Provisional Application 61/257,422, filed Nov. 2, 2009. This application is also a continuation of U.S. application Ser. No. 13/954,834, filed Jul. 30, 2013, now abandoned, which is a continuation-in-part of U.S. application Ser. No. 13/503,657, filed Apr. 24, 2012, now U.S. Pat. No. 8,604,067, which is a national stage application of PCT/US2010/052729, filed Oct. 14, 2010, which claims priority from U.S. Provisional Application 61/257,422, filed Nov. 2, 2009. The contents of the aforementioned priority applications are incorporated herein by reference in their entirety.

TECHNICAL FIELD

The presently disclosed invention relates to a method of cancer treatment using 2-(1'H-indole-3'-carbonyl)-thiazole-4-carboxylic acid methyl ester ("ITE") or one of its structural analogs. More particularly, the present invention provides a method by administering a therapeutically effective amount of ITE or one of its structural analogs to treat cancer in a subject in need thereof including prostate, liver, lung, ovarian, breast, skin, colorectal, stomach, pancreatic, kidney, bladder, soft tissue, and cervical cancer.

BACKGROUND OF THE INVENTION

The aryl hydrocarbon (Ah) receptor (AhR) is a ligand inducible transcription factor, a member of the basic helix-loop-helix/Per-Arnt-Sim (bHLH/PAS) superfamily. Upon binding to its ligand, AhR mediates or interacts with a series of biological processes as well as some adverse effects including cell division, apoptosis, cell differentiation, actions of estrogen and androgen, adipose differentiation, hypothalamus actions, angiogenesis, immune system homeostasis, teratogenicity, tumorigenicity, chloracne, wasting syndrome, and actions of other hormonal systems beside the expression of genes of P450 family and others. The liganded receptor participates in biological processes through translocation from cytoplasm into nucleus, heterodimerization with another factor named Ah receptor nuclear translocator, attachment of the heterodimer to the regulatory region termed Ah response element of genes under AhR regulation, and then either enhancement or inhibition of transcription of those genes.

The AhR happens to be able to bind, with different affinities, to several groups of exogenous chemicals (thus artificial ligands) such as polycyclic aromatic hydrocarbons exemplified by 3-methylchoranthrene (3-MC) and halogenated aromatic hydrocarbons typified by 2,3,7,8-tetrachlorodibenzo-p-dioxin (TCDD). The receptor system has been studied so far with its artificial ligands. While these studies helped greatly in advancing our understanding toward the receptor system, thorough elucidation of the physiological roles the system plays and the potential therapeutic benefits the system may offer are impossible without the identification of AhR physiological ligand. As the first step toward this goal, an endogenous ligand for the receptor has been identified. The endogenous ligand, or physiological ligand, or natural hormone, for the AhR was identified as 2-(1'H-indole-3'-carbonyl)-thiazole-4-carboxylic acid methyl ester (short for ITE).

Even though most of the artificial ligands for AhR are environmental toxins and thus cannot be used as therapeutic agents, for the purpose of understanding functions of liganded AhR, its artificial ligands such as TCDD, 6-methyl-1,3,8-trichlorodibenzofuran (6-MCDF), 8-methyl-1,3,6-trichlorodibenzofuran (8-MCDF), and those derived from indole or tryptophan were used to reveal that the liganded AhR was able to inhibit the metastasis of prostate tumors in a strain of transgenic mice and the growth of carcinogen induced rat mammary tumors, human breast tumor cell xenografts, and tumors caused by gene mutations.

As a natural ligand for AhR, ITE is an excellent agent in targeting precisely and specifically the receptor. The consequence of the targeting, however, is unpredictable from the behaviors of those artificial ligands for AhR, with some results demonstrating anticancer potentials while others tumor initiation, promotion, and progression. As disclosed in a U.S. patent application Ser. No. 13/503,657, it is impossible to predict meaningfully what a newly identified ligand for AhR might do in terms of cancer biology. The same application also explained that, as an antiangiogenic agent, ITE would not be automatically qualified as an effective anticancer agent, either.

There are two serious problems with current cancer therapies in the market. The first is side effects and toxicity. The second is efficacy. Consequently, cancer is still the second leading cause of death in the United States and areas of the world.

The majority of current therapeutic agents for cancer, in both cytotoxic and noncytotoxic categories, are chemicals foreign to the human body. As a result, the body tries to reject the agents using metabolic methods available. Since the human body does not have a natural and safe way of metabolizing those foreign chemicals, some nonspecific oxidation reactions then are used as major means of metabolism. The consequence is that the metabolic processes generate chemically active intermediates or radicals, which will assault also normal cellular substances including, but not limited to, that of immune system's in the body, leading to side effects, toxicity, and weakened immune system. Since most of these agents were designed by humans, not nature, they have very high chances to bind to and interact with other cellular factors (including, but not limited to, receptors, enzymes, other proteins) than their expected targets in the body. These "off-target" bindings and interactions account for opportunities for side effects.

Thus, the effectiveness of cytotoxic agents for cancer therapy is limited by their indiscriminate toxicity to normal cells and tissues including, but not limited to, that of immune system's. The weakened immune system makes it impossible to launch an organized assault on cancer cells. The efficacy of noncytotoxic agents, which target specific functions important for the survival of cancer cells, is limited by their single mechanism based strategy. An important hallmark of cancer, however, is their constant genetic changes or mutations. Once a cancer cell changes into a state that it is no longer dependent on a specific function a therapeutic agent targets for survival, the efficacy of the agent will then be lost.

Therefore, there is an unmet medical need to develop a method of cancer treatment with fewer side-effects and higher efficacy, in addition to find methods to protect normal cells from injuries caused by cancer treatment. Further, it is also desirable to development methods of cancer treatment that can alleviate the complication as disclosed herein.

SUMMARY OF THE INVENTION

The present invention provides methods using therapeutic agents that assault cancers cells with multiple combating capabilities for sustained potency, help immune system at the same time to organize an orchestrated attack on cancers and clean up individual cancer cells for potential cancer eradication, and limit the chance of "off-target" interaction and metabolize itself safely for low side effect(s).

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed invention provides a method of cancer treatment including administering a therapeutically effective amount of 2-(1'H-indole-3'-carbonyl)-thiazole-4-carboxylic acid methyl ester or one of its structural analogs at a dose of between 1 mg/kg and 500 mg/kg to a subject. In some embodiments, the cancer is selected from a group consisting of skin, colorectal, stomach, pancreatic, kidney, bladder, soft tissue, and cervical cancer. The structure analog of 2-(1'H-indole-3'-carbonyl)-thiazole-4-carboxylic acid methyl ester has the following formula:

Structural Formula 4

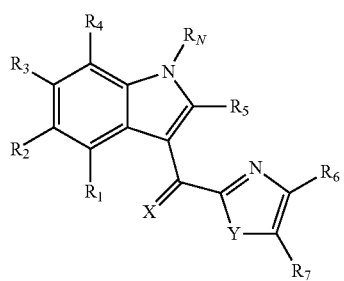

wherein
X and Y, independently, can be either O (oxygen) or S (sulfur);
$R_N$ can be selected from hydrogen, halo, cyano, formyl, alkyl, haloalkyl, alkenyl, alkynyl, alkanoyl, haloalkanoyl, or a nitrogen protective group;
$R_1$, $R_2$, $R_3$, $R_4$, and $R_5$ can be independently selected from hydrogen, halo, hydroxy (—OH), thiol (—SH), cyano (—CN), formyl (—CHO), alkyl, haloalkyl, alkenyl, alkynyl, amino, nitro (—NO$_2$), alkoxy, haloalkoxy, thioalkoxy, alkanoyl, haloalkanoyl, or carbonyloxy;

$R_6$ and $R_7$, can be independently selected from hydrogen, halo, hydroxy, thiol, cyano, formyl, alkyl, haloalkyl, alkenyl, alkynyl, amino, nitro, alkoxy, haloalkoxy, or thioalkoxy; or
$R_6$ and $R_7$, independently, can be:

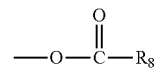

wherein $R_8$ can be selected from hydrogen, halo, cyano, alkyl, haloalkyl, alkenyl, or alkynyl; or $R_6$ and $R_7$, independently, can be:

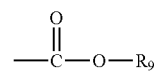

wherein $R_9$ can be selected from hydrogen, halo, alkyl, haloalkyl, alkenyl, or alkynyl; or $R_6$ and $R_7$, independently, can be:

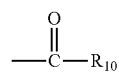

wherein $R_{10}$ can be selected from hydrogen, halo, hydroxy, thiol, cyano, alkyl, haloalkyl, alkenyl, alkynyl, amino, or nitro; or
$R_6$ and $R_7$, independently, can also be:

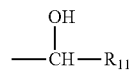

wherein $R_{11}$ can be selected from hydrogen, halo, alkyl, haloalkyl, alkenyl, or alkynyl.

In some embodiments, the structure of the 2-(1'H-indole-3'-carbonyl)-thiazole-4-carboxylic acid methyl ester is represented by the following structural formula:

Structural Formula 1

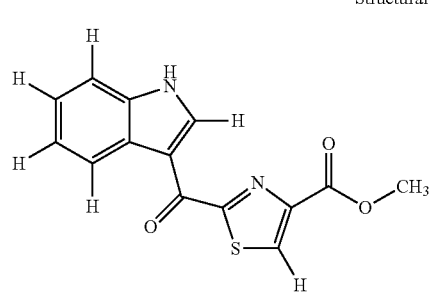

In some further embodiments, the structural analog of 2-(1'H-indole-3'-carbonyl)-thiazole-4-carboxylic acid methyl ester is represented by the following structural formula:

Structural Formula 2

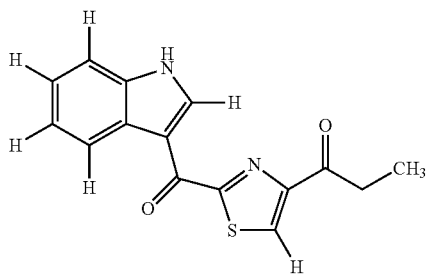

Yet in some embodiments, the structural analog of 2-(1'H-indole-3'-carbonyl)-thiazole-4-carboxylic acid methyl ester is represented by the following structural formula:

Structural Formula 3

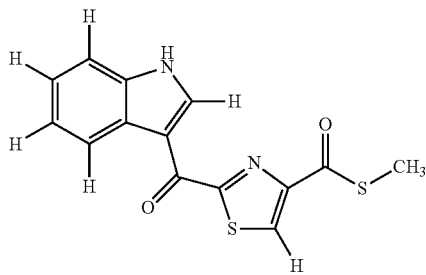

Further provided, in some embodiments, the 2-(1'H-indole-3'-carbonyl)-thiazole-4-carboxylic acid methyl ester or one of its structural analogs is combined with one or more pharmaceutically acceptable carriers to assist its administration to the subject. Yet in some embodiments, the 2-(1'H-indole-3'-carbonyl)-thiazole-4-carboxylic acid methyl ester or one of its structural analogs can be administered using topical, enteral, and parenteral application.

Still further provides, in some embodiments, the presently disclosed invention relates to a method that a dose of water is administered to the subject to reduce complication of dosing 2-(1'H-indole-3'-carbonyl)-thiazole-4-carboxylic acid methyl ester or one of its structural analogs. In some embodiments, the dose of water administered is in excess to normal water uptake by the subject. Yet in some embodiments, the dose of water is administered by oral injection.

In some embodiments of the presently disclosed invention, the 2-(1'H-indole-3'-carbonyl)-thiazole-4-carboxylic acid methyl ester or one of its structural analogs is administered together with one or more other cancer therapeutic agents to the subject.

In some embodiments of the presently disclosed invention, a maintenance dosing of the 2-(1'H-indole-3'-carbonyl)-thiazole-4-carboxylic acid methyl ester or one of its structural analogs is provided after the subject is free of cancer to ensure cancer eradication.

In some embodiments, the subject in need of treatment for cancer is a mammal. Yet in some embodiments, the mammal is a human.

Further provided, in some embodiments of the present invention, a subject is administered with the 2-(1'H-indole-3'-carbonyl)-thiazole-4-carboxylic acid methyl ester or one of its structural analogs once or twice daily.

In some cases, ITE or its structural analogs may cause feces hardening, rendering the passage of food and feces through intestinal system difficult. Thus, in some embodiments, the treatment methods of the present invention comprise administering an oral dose of water, in addition to normal water drinking to help alleviate feces hardening.

BRIEF DESCRIPTION OF THE FIGURES

FIGS. 1A-1D are graphs illustrating the growth inhibition of human cancer cell line LNCap xenografts in response to doses, routes, and schedules of ITE administration. FIG. 1A shows the degrees of growth inhibition of LNCaP xenografts (mean+SEM, n=8) in response to ITE doses of 0 (vehicle, DMSO), 0.1, 1, 10, 20, and 40 mg/kg b.w. (i.p. injection, every 12 hours for 28 continuous days). FIG. 1B shows the low toxicity response of the xenograft-bearing mice to the treatment judged by their body weight changes (mean+SEM, n=8). FIG. 1C shows PK (Pharmacokinetic) profiles of ITE administered (single dosing) i.v., i.p., and p.o. with vehicles used, dosing levels, and AUC's (Area under Curves) as indicated. FIG. 1D shows the inhibition of LNCaP xenograft growth by ITE at different doses (40 or 80 mg/kg b.w.), schedules (once or twice daily), and routes (i.p. or p.o.) of administration as specified.

FIG. 2A shows inhibition of LNCaP xenograft growth by ITE or ITK at 20 mg/kg for both. FIG. 2B shows growth inhibition of HepG2 xenografts by ITE or ITK at 80 mg/kg for both. FIG. 2C shows ITE or ITK inhibiting OVCAR-3 xenograft growth at a dose of 80 mg/kg for both, and wherein FIG. 2D shows a growth inhibition of MCF-7 xenografts by ITE at a dose of 20 mg/kg.

FIG. 3A shows aggressive growth of LLC tumors and ITE inhibition of tumor growth at a dose of 20 mg/kg. FIG. 3B shows a better inhibition of LLC tumor growth by ITE at 80 mg/kg (i.p. once daily) so that a treatment program of 28 days plus one more week of post injection observation could be finished. FIG. 3C shows one mouse (No. 33, diamond) from the ITE group (square) initiating its tumor shrinkage upon the start of the treatment phase, becoming tumor-free at day 13 in the treatment, keeping the tumor-free status during the rest of the treatment phase, and being still tumor-free in an entire one month of the observation phase. FIG. 3D shows body weight changes of mouse No. 33 (diamond) together with that of ITE (square) and vehicle control (circle) groups.

FIG. 4A shows the growth inhibition of A375 (skin cancer) xenografts (100-200 mg/kg). FIG. 4B shows the growth inhibition of M14 (skin cancer) xenografts (100-200 mg/kg). FIG. 4C shows the growth inhibition of HCT116 (colon cancer) xenografts (100-200 mg/kg). FIG. 4D shows the growth inhibition of SW116 (colon cancer) xenografts (100-200 mg/kg), and wherein FIG. 4E shows the growth inhibition of SGC7901

(stomach cancer) xenografts (100-200 mg/kg). FIG. 4F shows the growth inhibition of MFC (stomach cancer) homografts (200-300 mg/kg).

FIGS. 5A-5F are graphs illustrating the growth inhibition (mean+SEM, n=5) of cancer tissues derived from human and mouse cancer cells by ITE administration (i.p. injection, DMSO as vehicle, once daily continuous) at doses of 100-200 mg/kg (100 mg/kg first 10 days and 200 mg/kg then) or 200 mg/kg as indicated. FIG. 5A shows the growth inhibition of CFPAC-1 (pancreatic cancer) xenografts (100-200 mg/kg). FIG. 5B shows the growth inhibition of Ketr-3 (kidney cancer) xenografts (100-200 mg/kg). FIG. 5C shows the growth inhibition of T24 (bladder cancer) xenografts (100-200 mg/kg). FIG. 5D shows the growth inhibition of S180 (soft tissue cancer or sarcoma) homografts (200 mg/kg). FIG. 5E shows the growth inhibition of Siha (cervical cancer) xenografts (100-200 mg/kg). FIG. 5F shows the growth inhibition of U14 (cervical cancer) homografts (200 mg/kg).

DETAILED DESCRIPTION OF THE INVENTION

Figure 2B:
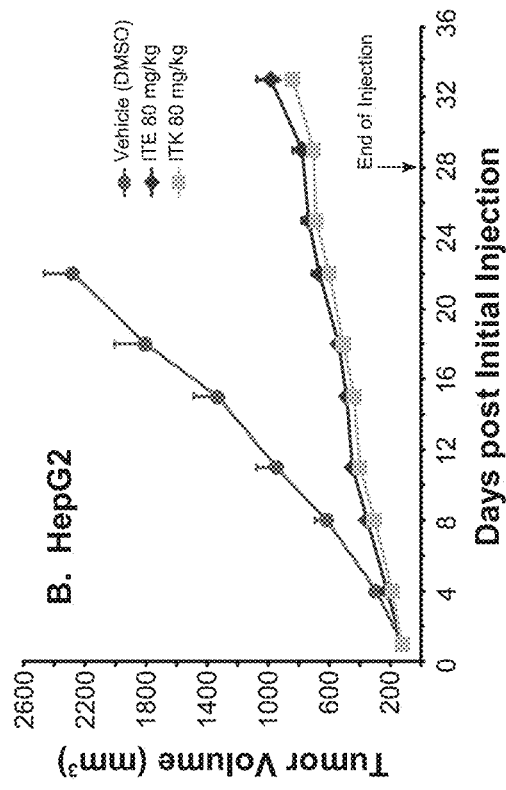
FIGS. 2A-2D are graphs illustrating ITE's (diamond) or ITK's (one of ITE structural analogs, square) efficacy in inhibiting the growth of xenografts of human prostate (LNCaP), liver (HepG2), ovarian (OVCAR-3), and breast (MCF-7) cancer cell lines (i.p. once daily).

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The most important advantage of the present invention is ITE's or one of its structural analogs' multiple cancer assaulting capabilities to defy the consequence of cancer cells' constant genetic changes.

As used herein, the term "Ah receptor" or "AhR" stands for a receptor named aryl hydrocarbon receptor, a ligand inducible transcription factor in biological systems. In literature, the Ah receptor (AhR) liganded with its artificial ligands was shown to be able to inhibit cell division, promote apoptosis, induce cell differentiation, and block actions of estrogen and androgen. Recently, AhR liganded with artificial ligands has been demonstrated to be able to induce the differentiation of immune T cells, useful for the immune system in organizing assault on pathogens and cancers. If ITE, or one of its structural analogs, when bound to AhR, can also have one or more of the functions mentioned plus its antiangiogenic capability, the multiple cancer assaulting capabilities may make its cancer therapeutic potency sustainable. The sustainability of the potency of ITE or one of its analogs plus its potential capability of stimulating the immune system to conduct precision attack on and individual clearing of cancer cells would not only enhance dramatically the efficacy of the cancer therapy but also make cancer eradication a possibility. The data presented herein clearly verify the theoretical analysis above.

A benefit of using ITE over others in the market is its possibility of low or no severe side effect(s) beside its sustainable efficacy backed by its multiple cancer assaulting capabilities. Contrary to those chemicals, including those AhR artificial ligands and most of agents used in current cancer therapies, foreign to human body and designed by humans, ITE is a natural hormone designed by the nature and so the nature may have designed and implemented a natural and safe way for its metabolism. Its metabolic process thus will cause less or even no problem to the body. This means that it may be low in side effect(s) caused by its metabolism. Another important reason for possible low side effect is that the binding of the natural hormone to its receptor (AhR) is supposed to be very specific and precise since it is designed by the nature, not humans. The natural hormone ITE, other than those human designed chemicals, will then have low chance of binding to and interacting with other cellular factors thus reducing or even eliminating "off-target" actions, important opportunities for side effects.

Another important issue in cancer therapy is that it is highly desirable for a therapeutic agent specifically working in cancer cells vs. normal cells to further enhance its potency and reduce side effects. This type of specificity can be achieved if there are more target molecules the agent binds in cancer cells than in normal cells. The target molecule for ITE and its analogs is AhR. In literature, AhR was reported to be highly concentrated in pancreatic cancer tissues from patients but very diluted in all normal pancreatic tissues examined. Similarly, the concentrated AhR is also documented with cancers of prostate, stomach, ovary, liver, lung, and esophagus. This means that the therapeutic specificity of ITE and its structural analogs could be achieved in these reported types of cancers at least.

The presently disclosed invention relates to a method of cancer treatment using 2-(1'H-indole-3'-carbonyl)-thiazole-4-carboxylic acid methyl ester ("ITE") or one of its structural analogs. Subjects with cancers of prostate, liver, lung, ovarian, and breast are preferably accepted for treatment. More particularly, the present invention provides a method by administering a therapeutically effective amount of ITE or one of its structural analogs to treat cancer in a subject in need thereof including skin, colorectal, stomach, pancreatic, kidney, bladder, soft tissue, and cervical cancer.

As used herein, the term "structural analog" or simply "analog" of ITE is defined as a compound with chemical structure similar to that of Ah receptor endogenous ligand ITE and with a capability of binding to the Ah receptor.

The term "treatment" or "treating" refers to curing or substantially curing a condition, as well as ameliorating at least one symptom of the condition, and are inclusive of prophylactic treatment and therapeutic treatment. As would be recognized by one of ordinary skill in the art, treatment that is administered prior to clinical manifestation of a condition then the treatment is prophylactic (i.e., it protects the subject against developing the condition). If the treatment is administered after manifestation of the condition, the treatment is therapeutic (i.e., it is intended to diminish, ameliorate, control, or maintain the existing condition and/or side effects associated with the condition). In some embodiments of the present invention, the terms further relate to cancer intervention or eradication, which means an action of reducing, inhibiting, or eliminating the illness or a pathological process or processes.

The term "therapeutically effective amount" is used herein to refer to an amount of the therapeutic agents (e.g., ITE or its structural analogs) sufficient to produce a measurable biological response (e.g., cancer intervention or eradication). Actual dosage levels of active ingredients in a therapeutic composition of the presently disclosed subject matter can be varied so as to administer an amount of the active compound(s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

The terms "subject," as used herein, refer to an individual to be treated by (e.g., administered) methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compound/compositions of the present invention (e.g., a composition for cancer treatment).

ITE or one of its analogs (the active ingredient) can be formulated with one or more pharmaceutically acceptable carrier.

As used herein, the term "pharmaceutically acceptable carrier" refers to inert materials useful for administering the active ingredient, preferably sterile and nontoxic. The carrier system should be compatible with the active ingredient and can be in a form of solid, liquid, or gas. The properly formulated active ingredient can then be administered topically, enterally, or parenterally to a subject with cancer. It can be provided, for example, in a form of cream, capsules, tablets, lozenges, or injectables. Other compatible ingredients such as preservatives, if needed, could be co-formulated with the active ingredient. It further refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

In some embodiments of the present invention, subjects with cancers of skin, colon (or rectum), stomach, pancreas, kidney, bladder, soft tissue, and cervix are treated with ITE or one of its structural analogs. Subjects with cancers of prostate, liver, lung, ovarian, and breast may also be treated. This is by no mean to limit the therapeutic scope, however. Given the multiple cancer assaulting capabilities that ITE and one of its analogs possess, plus the possibility of stimulation of a subject's immune system to precisely attack and clean up individual cancer cells for possible cancer eradication, the spectrum of the ITE therapy is envisioned to be further expanded.

Further provided, in some embodiments of the present invention, the effective dose range of ITE or one of its structural analogs is determined by measuring the subject's blood concentration of ITE or one of its structural analogs under a specified dosing regimen to establish a concentration-time profile, consulting with an established correlation between the similar concentration-time profiles and effects on cancer inhibition or eradication, which built during a trial or trials as that illustrated in the section of Examples, and balancing the therapeutic effects achievable with the possible toxicity to the subject and health condition or physical durability of the subject. The dosing frequency of ITE or one of its structural analogs is decided similarly as described for the determination of a dose range above. Currently, once a day administration either enterally or parenterally is proposed as preferable with ITE. The dosing will be continued until the subject is free from the cancer. It is preferable to provide a maintenance dosing, whose duration is directed by a trial or trials, after the subject is free of cancer to ensure its complete elimination or eradication.

In the preferred intervention program, extra water is administered orally, in addition to normal daily water drinking, to alleviate an ITE dosing complication due probably to the hardening of feces. A daily dose of 20 ml/kg of water administered orally in a short period of time is proposed preliminarily. An optimal dose level and schedule are determined by a trial or trials as illustrated in the section of Examples.

The term "complication" as used herein refers to a symptom associated with a disease or with a treatment process of a disease with effective amount of the therapeutic agents. A non-limiting example is dry or hardened feces in a subject in need of cancer treatment after administering effective amount of ITE or its analogs.

In some embodiments of the presently-disclosed invention, ITE or one of its structural analogs may be administered in combination with one or more of other cancer therapeutic agents, preferably aiming different therapeutic targets other than AhR. ITE or one of its structural analogs can be formulated either independently from or together with one or more of the other said agents. ITE or one of its structural analogs can be administered either at the same schedule with or different from that of one or more of the other said agents. The proportioning of ITE or one of its structural analogs to one or more of the other cancer therapeutic agents can be directed by a well-designed trial or trials. Combining the therapy of ITE or one of its analogs with one or more of the other cancer therapeutic agents, may further enhance the efficacy. There are lots of examples to show the benefits of combination therapy.

In some embodiments of the present invention, the active ingredient is the aryl hydrocarbon (Ah) receptor (AhR) endogenous ligand ITE with the following structural formula (Structural Formula 1):

Structural Formula 1

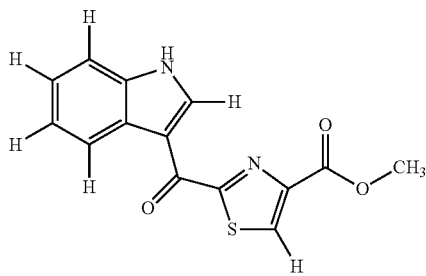

In some other embodiments, the active ingredient can be selected from two especially useful structural analogs of ITE. The said two analogs are envisioned to increase their stability and then extend their half-life in the subjects' systems since either a ketone or thiol ester functional group replaces the normal (oxygen) ester, targeted easily by numerous esterases in biological systems, in the structure of ITE. The extended half-life may translate into higher efficacy and/or longer duration of potency in cancer intervention. The ketone analog (thus termed ITK) of ITE is of the following structural formula (Structural Formula 2):

Structural Formula 2

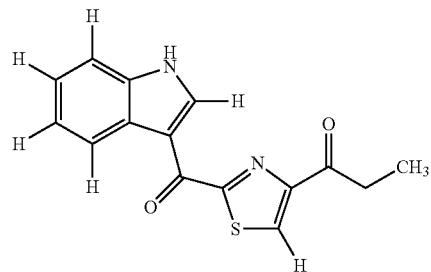

Whereas the structural formula of the thiol (S, sulfur) ester analog (thus termed ITSE) of ITE is as follows (Structural Formula 3):

Structural Formula 3

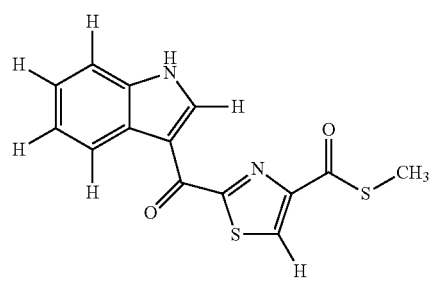

In some embodiments, the active ingredient can be further selected from the other structural analogs of ITE, specified by the following structural formula (Structural Formula 4):

Structural Formula 4

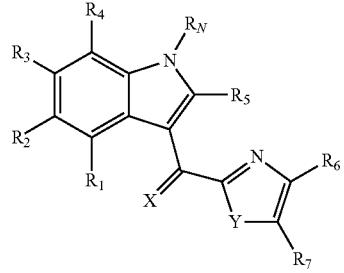

wherein

X and Y, independently, can be either O (oxygen) or S (sulfur);

$R_N$ can be selected from hydrogen, halo, cyano, formyl, alkyl, haloalkyl, alkenyl, alkynyl, alkanoyl, haloalkanoyl, or a nitrogen protective group;

$R_1$, $R_2$, $R_3$, $R_4$, and $R_5$ can be independently selected from hydrogen, halo, hydroxy (—OH), thiol (—SH), cyano (—CN), formyl (—CHO), alkyl, haloalkyl, alkenyl, alkynyl, amino, nitro (—NO$_2$), alkoxy, haloalkoxy, thioalkoxy, alkanoyl, haloalkanoyl, or carbonyloxy;

$R_6$ and $R_7$, can be independently selected from hydrogen, halo, hydroxy, thiol, cyano, formyl, alkyl, haloalkyl, alkenyl, alkynyl, amino, nitro, alkoxy, haloalkoxy, or thioalkoxy; or $R_6$ and $R_7$, independently, can be:

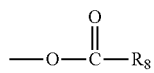

wherein $R_8$ can be selected from hydrogen, halo, cyano, alkyl, haloalkyl, alkenyl, or alkynyl; or
$R_6$ and $R_7$, independently, can be:

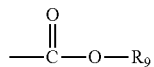

wherein $R_9$ can be selected from hydrogen, halo, alkyl, haloalkyl, alkenyl, or alkynyl; or
$R_6$ and $R_7$, independently, can be:

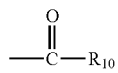

wherein $R_{10}$ can be selected from hydrogen, halo, hydroxy, thiol, cyano, alkyl, haloalkyl, alkenyl, alkynyl, amino, or nitro; or
$R_6$ and $R_7$, independently, can also be:

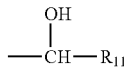

wherein $R_{11}$ can be selected from hydrogen, halo, alkyl, haloalkyl, alkenyl, or alkynyl.

As used herein, the term "alkyl" represents a group of hydrogen saturated one to six carbons connected in either straight or branched fashion.

As used herein, the term "haloalkyl" represents an alkyl substituted by one or more halogen atoms.

As used herein, the term "alkenyl" represents a group of hydrocarbons containing two to six carbons connected in either straight or branched fashion with at least one carbon-to-carbon double bond.

As used herein, the term "alkynyl" represents a group of hydrocarbons containing two to six carbons connected in either straight or branched fashion with at least one carbon-to-carbon triple bond.

As used herein, the term "halo" represents any of halogen atoms (F, Cl, Br, or I).

As used herein, the term "carbonyl" represents:

As used herein, the term "alkanoyl" represents an alkyl connected to a carbonyl group:

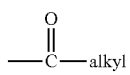

As used herein, the term "haloalkanoyl" represents a haloalkyl connected to a carbonyl group:

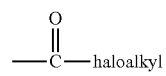

As used herein, the term "nitrogen protective group" represents groups commonly used to protect nitrogen from undesired chemical reactions during synthesis procedures.

As used herein, the term "amino" represents —NRaRb where Ra and Rb can be independently selected from hydrogen, halo, formyl (—CHO), alkyl, haloalkyl, alkenyl, alkynyl, alkanoyl, haloalkanoyl, or a nitrogen protective group.

As used herein, the term "alkoxy" represents an alkyl connected to an oxygen atom (—O-alkyl).

As used herein, the term "haloalkoxy" represents a haloalkyl connected to an oxygen atom (—O-haloalkyl)

As used herein, the term "thioalkoxy" represents an alkyl connected to a sulfur atom (—S-alkyl).

As used herein, the term "carbonyloxy" represents an alkanoyl connected to an oxygen atom:

The presently-disclosed subject matter is further illustrated by the following specific but non-limiting examples. Some of the following examples are prophetic, notwithstanding the numerical values, results and/or data referred to and contained in the examples.

EXAMPLES

Examples from animal studies will further help the embodiment of the present invention. Use of ITE in inhibition of human prostate cancer growth (Example 1), use of ITE or ITK (one of ITE analogs) in inhibiting the growth of more human cancer types (Example 2), use of ITE in possible cancer eradication (Example 3), ITE toxicity monitoring (Example 4), use of orally administered water, in addition to normal water drinking, to alleviate ITE dosing complication, and use of ITE in inhibiting growth of cancers originated from varieties of organs in both human and mouse (Example 5) will be demonstrated.

Example 1

Materials

Male BALB/c nude mice (*Mus musculus*), 6 to 8 weeks of age, were individually marked by ear coding. The animals were kept in laminar flow rooms at a constant temperature of 20 to 26° C. and humidity of 40 to 70% with 1 animal in each polycarbonate cage (300 mm×180 mm×150 mm). The bedding material was corn cob, which was changed twice weekly. Animals had free access to sterile dry granule food and sterile drinking water during the entire study.

ITE was synthesized by KNC Laboratories Co., Ltd. (Tokyo, Japan). The lot number of the compound is 086-009-2-1 (as lot No.: AHR-001 for AhR Pharmaceuticals). The DMSO (Cat. No.: 0231-500ML) was manufactured by AMRESCO (Solon, Ohio, USA). The Labrasol was purchased from Gattefosse (Saint-Priest, France) and the PEG 400 was supplied by Sigma (St. Louise, Mo., USA).

Methods

1. Efficacy Studies

All the procedures related to animal handling, care, and the treatment in the study were performed following guidelines approved by an Institutional Animal Care and Use Committee (IACUC) of Crown Bioscience, Inc. (Santa Clara, Calif., USA, a contract research organization we hired) based on the guidance of the Association for Assessment and Accreditation of Laboratory Animal Care (AAALAC). Animals were checked for any effects of tumor growth and drug treatment on normal behavior such as mobility, food and water consumption, body weight gain/loss (gross body weights were measured twice weekly), eye/hair matting, and any other abnormal effect. Death and observed clinical signs were recorded on the basis of the number of animals within each group. Individual animals with a tumor volume exceeding 3,000 mm$^3$ or animals of a group with a mean tumor volume exceeding 2,000 mm$^3$ were euthanized. In addition, animals showing signs of severe distress and/or pain, dropping body weight more than 20% from that at the start of treatment, or losing the capability of accessing adequate food or water were humanely sacrificed.

The human prostate cancer cell line LNCaP (ATCC, American Type Culture Collection, Manassas, Va., USA) were maintained in vitro as monolayer culture in RPMI-1640 medium supplemented with 10% fetal bovine serum (FBS), 100 U/ml penicillin, 100 μg/ml streptomycin, and 2 mM L-glutamine at 37° C. in an atmosphere of 5% $CO_2$ in air. The tumor cells were routinely subcultured twice a week. The cells growing in an exponential phase were harvested and counted for tumor inoculation.

Each mouse was inoculated subcutaneously at the right flank with the LNCaP cells (1×10$^7$) in 0.1 ml of PBS for tumor development. When a mean tumor volume reached around 150 mm$^3$, the tumor-bearing mice were divided into homogeneous blocks based on their tumor volumes followed by a randomization of mice in each block into treatment groups (thus minimizing variations in tumor response to treatments due to the differential in initial mean tumor volumes). Each treatment group was consisted of 8 tumor-bearing mice. Vehicle (DMSO) or ITE in the vehicle at specified doses were administered to the mice by either i.p. (intraperitoneal) or p.o. (oral) injection once or twice daily for 28 continuous days as indicated.

Tumor volume was measured twice weekly in two dimensions using a caliper and the volume was calculated with a formula of: $V=0.5\ a \times b^2$, where a and b are the long and short diameter (in mm) of a tumor, respectively. The tumor volume was then used for calculations of both TGI (Tumor Growth Inhibition) and TGD (Tumor Growth Delay). The TGI was determined by: TGI=ΔT/ΔC×100%, where ΔT was a difference between the mean tumor volume at a specified day of observation and that at the day treatment starts (day 1) for a drug treated group whereas ΔC was the same difference measured for the control group. The TGD was calculated as: TGD=T−C, where T was the time (in days) required for tumors in a drug treated group to reach a predetermined mean tumor volume and C the time (in days) in the control group to reach the same volume. A tumor weight was derived by equating 1,000 mm$^3$ in volume to 1,000 mg in weight. A net body weight was then derived by subtracting a tumor weight from a corresponding gross body weight with the tumor.

Summary statistics, including mean and the standard error of the mean (SEM), are provided for the tumor volume of each group at each time point. Statistical analysis of difference in tumor volume among groups was conducted on a data set either at the best therapeutic time point or at the final dosing day as indicated. The tumor volume data were log-transformed and evaluated using a one-way ANOVA followed by Tukey's test when significance was observed. All data were analyzed using SPSS 16.0 and p<0.05 was considered to be statistically significant.

2. PK Studies

Male nude mice were also used in PK (pharmacokinetic) studies. For i.v. injection, ITE at 1 mg/kg b.w. was administered with DMSO as vehicle via tail vein. For i.p. Injection, ITE at 10, 40, and 80 mg/kg b.w. was delivered with DMSO via lower left abdominal quadrant. In p.o. injection, ITE at 40 and 80 mg/kg b.w. were administered with a vehicle of Labrasol:PEG 400 (2:8, v/v) via oral gavage. Every 15 mice were given a single injection at each dosing level and every 3 of the dosed mice were used to collect blood sample at each time point (0, 0.083, 0.25, 0.5, 1, 2, 4, 8, 24 hr.). Animals were rotated to be sampled twice each but the duration between the two sampling times was at least 110 min. The animal was anesthetized under Isoflurane and restrained manually. Approximately 150 μl of whole blood at each time point is collected (via retro-orbital puncture) into a $K_2$-EDTA tube. Blood samples were put on ice and processed to plasma (4,000 g, 5 min, 4° C.) within 15 min post sampling. Plasma samples were stored at −80° C. until analysis. An aliquot of 20 μl plasma sample was added with 20 μl of an internal standard (Glipizide, 500 ng/ml in ΔCN, for extraction efficiency) to 120 μl of ΔCN (acetonitrile). The mixture was vortexed at 1,500 rpm for 2 min. and then centrifuged at 12,000 rpm for 5 min. Five (5) μl of the supernatant was injected into an LC-MS/MS system (API 4000, Foster City, Calif., USA). A Gemini-C18 column (2.0×50 mm, 5 μm) was used and the LC (liquid chromatography) was run at a flow rate of 0.45 ml/min. with the following program:

| Time (min) | 0.0 | 0.2 | 1.8 | 2.8 | 2.9 | 4.0 |
|---|---|---|---|---|---|---|
| Pump A (%) | 95 | 95 | 2 | 2 | 95 | Stop |
| Pump B (%) | 5.0 | 5.0 | 98 | 98 | 5.0 | Stop | where Pump A was for 1 mM $NH_4OAc$ (ammonium acetate) in water plus 0.025% FA (formic acid) whereas Pump B for 1 mM $NH_4OAC$ in acetonitrile plus 0.025% FA. The negative ionization process of the mass spectrometry was operated at an APCI (Atmospheric Pressure Chemical Ionization) mode while the detection at a MRM (Multiple Reaction Monitoring) mode. ITE was identified by recognizing an LC retention time of 2.5 min. and two mass peaks at 285.0 (before collision) and 142.0 m/z (after collision) while the internal standard of 2.35 min. and two mass peaks at 444.3 (before collision) and 319.3 m/z (after collision). ITE was quantified by a standard curve generated every time by a series of known quantities of ITE running through both the extraction/precipitation process after mixing with mouse plasma and the LC-MS/MS system. The WinNonlin V5.2 statistics software (Pharsight Corporation, California, USA) was used to generate PK parameters such as $C_{max}$, $T_{max}$, $T_{1/2}$, and AUC (Area under Curve) etc. using a non-compartmental model.

Results

Treatment with ITE at doses of 1, 10, 20, and 40 mg/kg b.w. (i.p., every 12 hr. for 28 continuous days, DMSO as vehicle, 0.5 ml/kg b.w. as injection volume) produced significant anticancer activities with a clear dose-effect relationship (FIG. 1A). The TGI's (Tumor Growth Inhibition) were calculated as 52%, 31%, 26%, and 22% at day 28 (n=8; p<0.048, 0.007, 0.004, and 0.004), respectively, for the dosing series. The TGD (Tumor Growth Delays) of 3, 10, 12, and 16 days, respectively, at a tumor size of 600 mm$^3$ were attained by the series. ITE at 0.1 mg/kg b.w. didn't produce a statistically significant anticancer activity (n=8, TGI=74% at day 28, p<0.623). Judging from the body weight changes of the tumor-bearing mice, ITE treatment did not seem to provoke significant toxic response (FIG. 1B).

To understand pharmacokinetic (PK) behavior of ITE and direct further efficacy studies, ITE was administered to nude mice in different routes and at different levels. ITE PK profiles are depicted in FIG. 1C. ITE in DMSO at 1 mg/kg b.w. delivered by a bolus i.v. injection was degraded very quickly with an estimated half-life of 6 min. An estimated AUC for the route was 256 hr·ng/ml. ITE in DMSO administered by i.p. injection improved its half-life while the efficiency of absorption was below 10% compared with that of i.v. injection. For example, ITE half-life for 10, 40, and 80 mg/kg b.w. of i.p. injection were 1.13, 1.61, and 5.17 hr., respectively, while AUC for the series was 197, 332, 499 hr·ng/ml, respectively. ITE in Labrasol:PEG 400 (2:8, v/v) delivered via p.o. route had even lower absorption efficiency (around 1%) while kept the half-life to the levels that achieved by i.p. injection. The AUC for the dosing levels of 40 and 80 mg/kg b.w. of p.o. injection was 107 and 97 hr·ng/ml, respectively (FIG. 1C).

Based on the results from PK studies, the schedule, dosing level, and routes of ITE administration were further explored. When a total daily dose was kept the same, the dosing schedule of either once or twice daily for the i.p. route resulted in comparable efficacy in inhibition of cancer growth (e.g. 80 once vs. 40 mg/kg b.w. twice daily, FIG. 1D). Further raising ITE dose to 80 mg/kg (twice daily, i.p.) seemed to further improve the TGI from that of 40 mg/kg (twice daily, i.p.). TGI for 80 mg/kg (twice daily, i.p.) were the best so far obtained, 12% at day 28 and 16% at the last day, for example. Even though absorption efficiency of ITE via p.o. route at a dose of 80 mg/kg was much lower than that of 10 mg/kg i.p. in terms of AUC (FIG. 1C), 80 mg/kg p.o. daily was similar to that of 40 mg/kg i.p. daily in terms of cancer growth inhibition (TGI=46% at day 24, for example) during the first three weeks or so. From the PK studies, ITE plasma level of 80 mg/kg p.o. was lower than that of 10 mg/kg i.p. at the initial hours but became higher than that of 10 mg/kg i.p. and even 40 mg/kg i.p. during hour 3 to 8 post injection (FIG. 1C). That may be the reason behind the results of p.o. injection during the first three weeks. For the p.o. injection, its therapeutic efficacy somehow would not hold longer than that of i.p. injections toward and post the end of treatment (FIG. 1D).

Example 2

Materials and Methods

The culture and inoculation of human prostate cancer cell line LNCaP were as described in Example 1. The manipulation for human liver cancer cell line HepG2 (ATCC) was similar as that for LNCaP except that DMEM (instead of RPMI-1640) medium was used, the L-glutamine was not used, and $2 \times 10^6$ cells were used for inoculation into female nude mice. The handling of human ovarian cancer cell line OVCAR-3 (ATCC) was the same as that of LNCaP except that the DMEM medium was used and $5 \times 10^6$ cells were used for inoculation into female nude mice. The human breast cancer cell line MCF-7 (CL-161) is a cloned line from MCF-7 (ATCC) and the growth of its xenografts no longer needs exogenous supply of estrogen. The culture of the MCF-7 cells was similar as that of LNCaP except that MEM medium supplemented with 1 mM non-essential amino acids, 1 mM sodium pyruvate, and 0.01 mg/ml bovine insulin was used to replace RPMI-1640 medium. The inoculation of MCF-7 cells was the same as that of LNCaP except that 0.1 ml of PBS with Matrigel (1:1) and female mice were used for tumor development.

Source of ITE is the same as that described in Example 1. The compound ITK (Structural Formula 2), one of ITE structural analogs, was synthesized by Shanghai ChemPartner Co., Ltd. (Shanghai, China). The lot number was: AhR-ITK-001.

Results

ITK (one of ITE structural analogs) was shown to be efficacious at 20 mg/kg b.w. (i.p. once daily) and performed even better than ITE in the same regimen in human prostate cancer (LNCaP) xenograft model (FIG. 2A). The TGI's (Tumor Growth Inhibition) were 51% (p<0.003, n=8) and 64% (p<0.021, n=8) for ITK and ITE, respectively, at day 28. The TGD's (Tumor Growth Delay) for ITK and ITE were 16 and 8 days, respectively, at a tumor volume of 1,000 $mm^3$.

Both ITE and ITK at 80 mg/kg (i.p. once daily) demonstrated good efficacy in inhibiting the growth of human liver cancer (HepG2) xenografts. The performance of ITE and ITK was very comparable in this model (FIG. 2B). The TGI's for ITE and ITK were 25% (p<0.001, n=8) and 22% (p<0.001, n=8), respectively, at day 22. The TGD's were 29 and 26 days at a tumor volume of 800 $mm^3$ for ITE and ITK, respectively. There was no obvious net body weight loss (data not shown) even though there was 1 out of 8 mice in ITK group died at day 32.

Figure 2D:
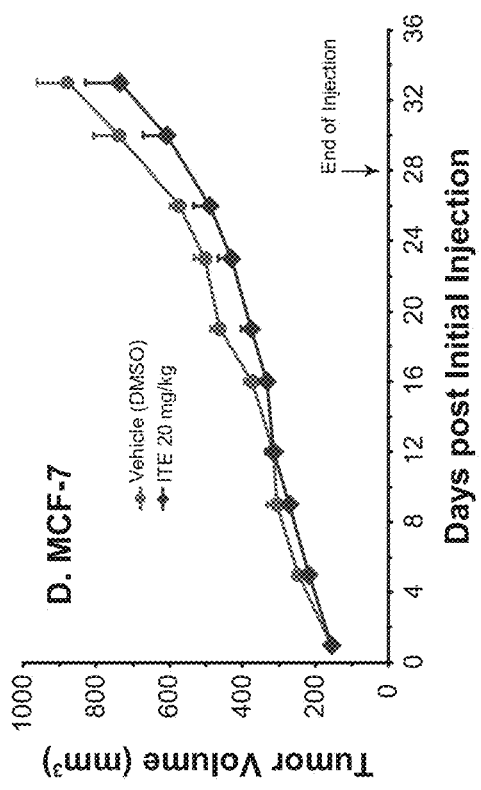
Figure 2A:
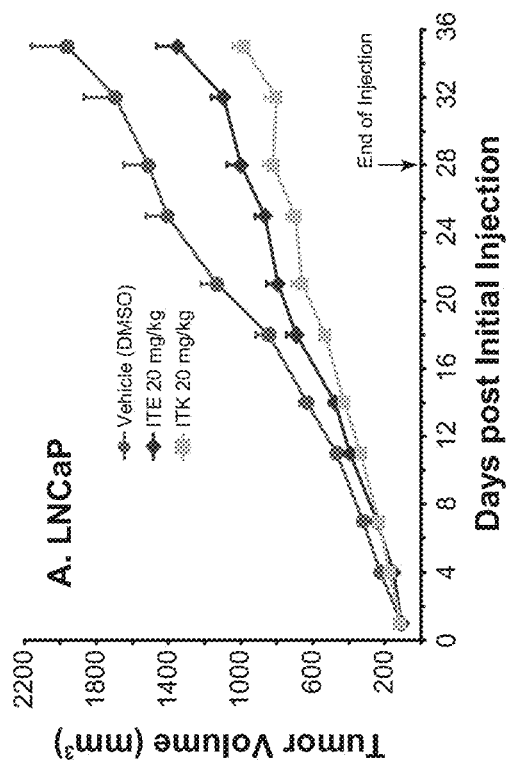
Figure 2C:
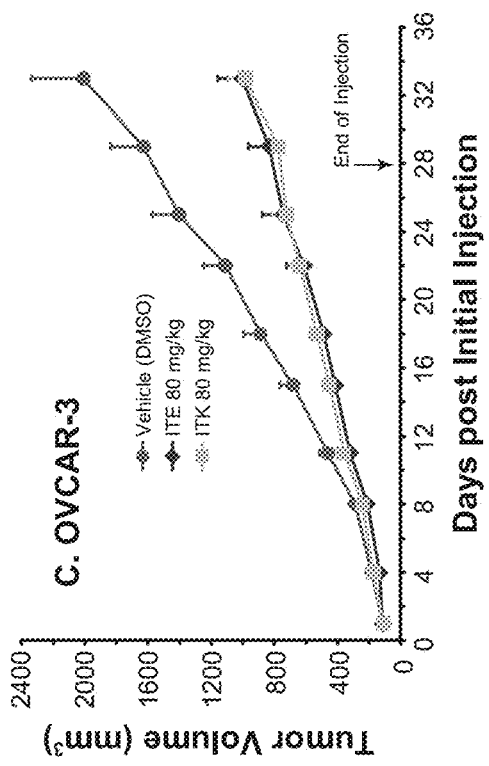

Both ITE and ITK at 80 mg/kg (i.p. once daily) again demonstrated a similar efficacy in inhibiting human ovarian cancer (OVCAR-3) growth (FIG. 2C). The TGI's were 47% (p<0.002, n=8) and 46% (p<0.001, n=8) at day 33 for ITE and ITK, respectively. The TGD's for ITE and ITK were, respectively, 10 and 13 days at a tumor volume of 800 $mm^3$. There was no obvious net body weight loss (data not shown). There was again 1 out of 8 mice in ITK group died also at day 32.

ITE displayed a modest efficacy, albeit at a modest dose (20 mg/kg, i.p. once daily), in inhibiting human breast cancer (MCF-7) growth (FIG. 2D). A TGI was calculated as 71% (p<0.031, n=8) at day 19 for the ITE treatment. A TGD of 3 days at a tumor volume of 500 $mm^3$ was obtained for ITE group. Further increase in dosing levels is certainly needed to yield a better growth inhibition and delay but the response of MCF-7 xenografts to ITE treatment was there.

The performance of one of ITE structural analogs (ITK) in this Example validates a huge potential of ITE analog development based on a framework specified by the Structural Formula 4. In addition, an analog with a thiol ester functional group replacing the normal (oxygen) ester in the ITE structure is envisioned to be specially important given the results of ITK (Structural Formula 2) studies. The thiol (S, sulfur) ester so specified by the Structural Formula 3 is thus abbreviated as ITSE. The structural feature of both ITK and ITSE may help fend against attacks by numerous esterases in biological systems specifically to the oxygen ester functional group on the structure of ITE.

Example 3

Materials and Methods

Murine Lewis lung cancer cell line LLC (ATCC) was cultured as described for LNCaP in Example 1 except DMEM, instead of RPMI-1640, medium being used. Each female C57BL/6 mice, 6 to 8 weeks of age, was inoculated with $3\times10^5$ LLC cells in 0.1 ml of PBS for tumor development. ITE treatment was started when a mean tumor volume reached 80 to 120 $mm^3$. All the other materials and methodologies were the same as that described in Example 1.

Results

Figure 3A:
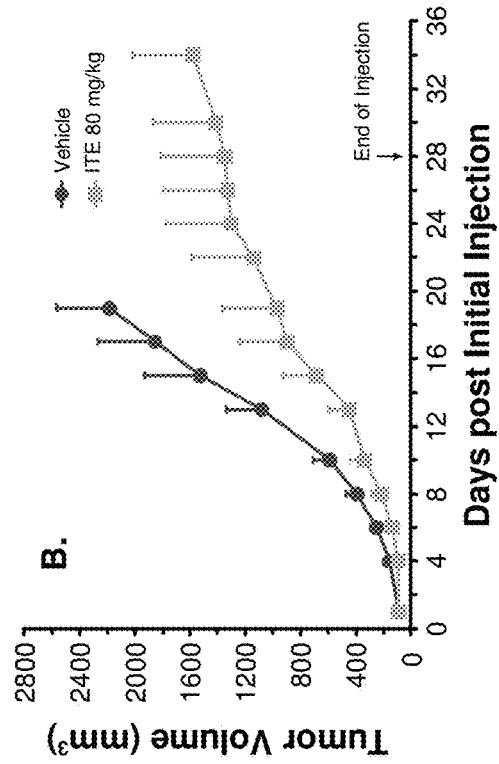
FIGS. 3A-3D are graphs illustrating cancer inhibition and eradication by ITE (i.p. once daily) in a syngeneic murine Lewis lung cancer (LLC) model.

The benefit of using xenograft model is that human cancers can be directly tested on animals. The disadvantage, however, is that the mice have to have defects in their immune systems so that they will not reject human cancer cells. It is obvious, therefore, that this type of models cannot be used to test if ITE can stimulate immune system to dramatically enhance its therapy. A syngeneic model, mouse tumor cells inoculated to mice with healthy immune systems, was then used. At a dose of 20 mg/kg b.w. (i.p. once daily), while ITE showed a growth inhibition of the mouse lung cancer (n=8, TGI=65% at day 15, FIG. 3A), there was no indication of cancer elimination or eradication. In fact, the tumor growth was so aggressive in this model that the experiment had to be stopped earlier to relieve the suffering of animals in both control and ITE groups from heavy tumor burdens.

Figure 3B:
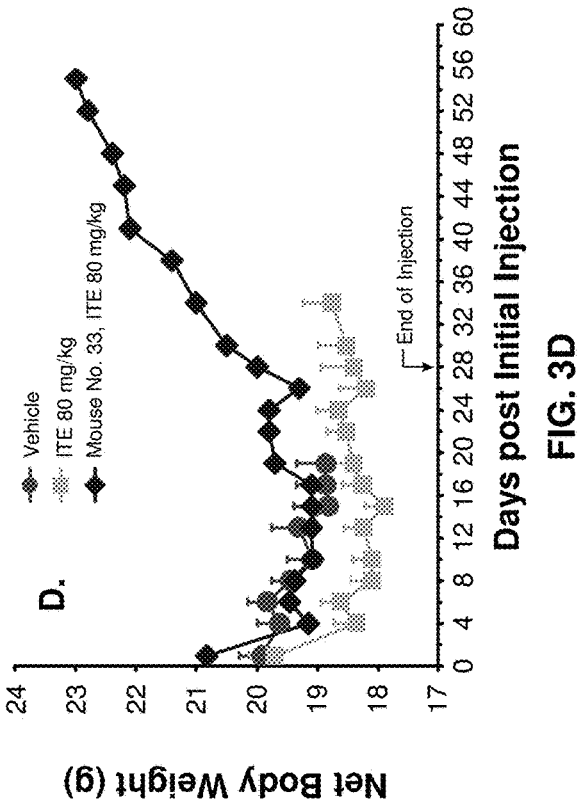
Figure 3C:
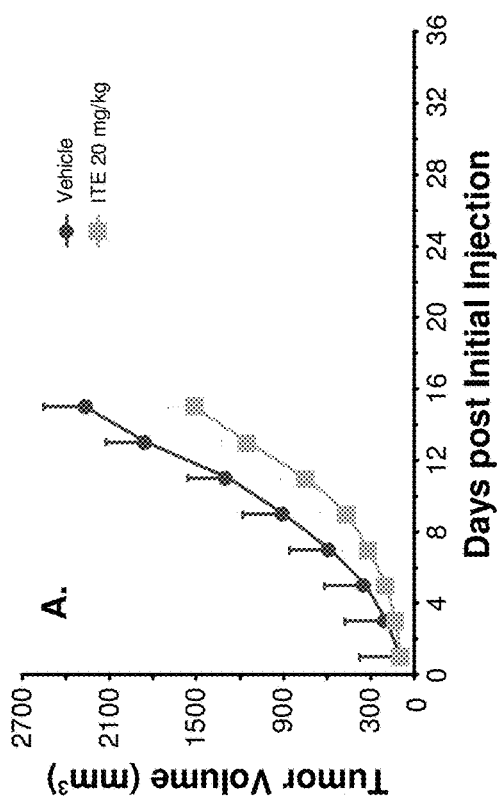
Figure 3D:
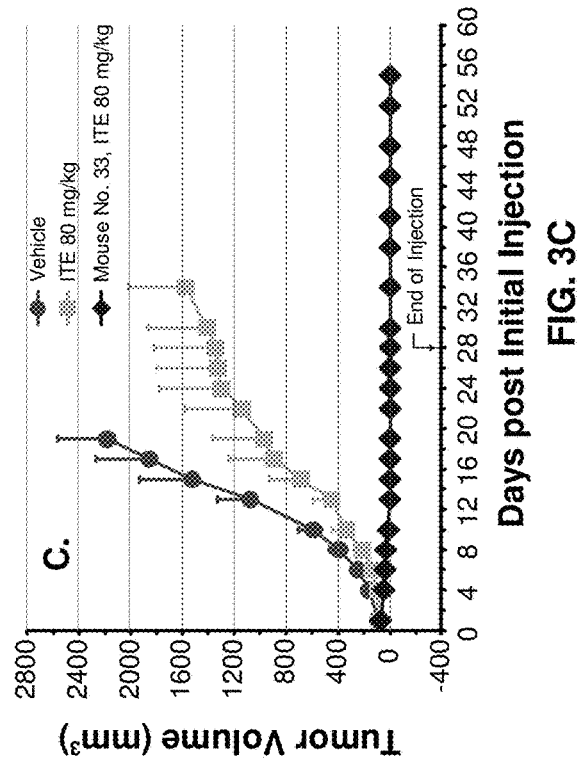

At a dose of 80 mg/kg b.w. (i.p. once daily), ITE significantly improved the growth inhibition of tumors so that ITE treated group could then be kept to the end of the experiment without early termination (FIG. 3B) like before. The TGI at day 20 for ITE treatment was 42% (n=8, p<0.037) and TGD at a tumor volume of 1000 $mm^3$ was 7 days. One of the mice in ITE group (mouse No. 33) started to shrink its tumor upon the start of ITE treatment and kept doing so until its tumor was no longer palpable at day 13 (FIG. 3C). The mouse kept tumor free during the rest of the ITE treatment phase (total 28 days). One more month was then given to the mouse after the stop of the 28-day treatment to show possible regrowth of its tumor. But that did not happen and the mouse kept tumor free during the entire month of observation, suggesting the elimination of every cancer cell by the treatment (FIG. 3C). Body weight change monitoring indicated the mouse No. 33 and the other mice in ITE group tolerated well to the treatment (FIG. 3D).

With xenograft models, complete tumor elimination has never happened at a dose of 80 mg/kg b.w. (i.p. once daily) or even at 80 mg/kg dosed (i.p.) twice a day. That may argue for the stimulation of immune systems in mice of this syngeneic model.

Actually, results in Example 4 below may also support this notion by showing increased counts of white blood cells, neutrophils, lymphocytes, and platelets at high (500 mg/kg, i.p. once daily) and mid (100 mg/kg, i.p. once daily) but not low (20 mg/kg, i.p. once daily) dose. Cancer eradication thus may be achieved if immune system could be mobilized to help fighting cancers and cleaning up individual cancer cells while cancer growth could be effectively inhibited and assaulted at the same time.

Example 4

Materials and Methods

ITE nano-suspension was prepared by milling ITE powder in water containing 1% CMC-Na (sodium carboxymethyl cellulose), 0.5% SLS (sodium lauryl sulfate), 0.085% PVP K90 (polyvinylpyrrolidone K90), and 0.2% Benzoate with a Media Wet Milling Machine (Dispermat SL-nano, WAB Willy A. Bachofen A G, Muttenz, Switzerland) until reached a desired size range. The particle size was determined by a Laser Diffraction Particle Size Analyzer (MS2000, Malvern Instruments, Worcestershire, UK). The parameters of particle sizes were determined as D10 (diameter of 10% of particles)=67 nm, D50=114 nm, and D90=207 nm. The nano-suspension thus prepared was stored at 4° C. until use.

Female C57BL/6 mice, 6 to 8 week old, were randomly assigned to 4 dose groups (0, 20, 100, and 500 mg/kg b.w.) each with 6 animals. ITE nano-suspension was administered by i.p. injection once daily for 7 consecutive days. Mortality, clinical signs, body weight, and food consumption were recorded. Data on hematology (3 of 6 mice) and serum chemistry (the other 3 of 6 mice) were collected. TK (Toxicokinetic) parameters were determined as described in Example 1 and plasma levels of ITE at both 1 and 3 hr. post dosing on day 1, 3, and 7 were measured. A gross observation of major organs at necropsy was conducted.

Results

TK data confirmed the proper ITE system exposure (data not shown). There was no mortality observed except that one mouse in 20 mg/kg b.w. (low dose) group died without known cause before the second day of dosing. There was no significant body weight loss due to ITE treatments even though a dramatic decrease in food consumption in all 3 ITE treated groups was noticed at day 1 of the study. No abnormality was observed from major organ inspection of all the ITE treated groups at necropsy. Levels of ALT (alanine aminotransferase), AST (aspartate aminotransferase), and TP (total protein) of 500 mg/kg (high dose) group was raised by 3.2 (p<0.05), 1.8 (not significant), and 1.2 (p<0.05) folds, respectively, over vehicle control (Table 1). BUN (blood urea nitrogen) of 20 mg/kg (low dose) group was raised by 1.4 folds (p<0.05) over vehicle. These data, especially those of ALT, may suggest an approaching near to the up limit of ITE dosing. WBC (white blood cell count) was raised by 2.6 (p<0.05) and 2.0 folds (not significant) for 100 (mid) and 500 mg/kg (high) group, respectively. Others like percentage of PLT (platelets), percentage of NEUT (neutrophils), numbers of neutrophils (# NEUT), and numbers of lymphocytes (# LYMPH) were increased in both 100 and 500 mg/kg groups albeit not statistically significant (Table 1). Data in hematology, even though more confirmatory studies need to be done, may actually suggest the mobilization of the immune system by ITE, thus reverberating probably to the data of cancer eradication presented in Example 3.

TABLE 1

Partial readings on hematology and serum chemistry

| Dose (mg/kg) | ALT (U/L) | AST (U/L) | BUN (mmol/L) | TP (g/L) | WBC ($\times 10^9$ cells) | PLT ($\times 10^9$ cells) | NEUT (%) | #NEUT ($\times 10^9$ cells) | #LYMPH ($\times 10^9$ cells) |
|---|---|---|---|---|---|---|---|---|---|
| 0 | 23.6 (6.4) | 84.3 (37.9) | 7.6 (1.2) | 39.7 (3.3) | 4.22 (1.85) | 539 (218) | 19.4 (4) | 0.87 (0.67) | 3.09 (1.82) |
| 20 | 43.2 (43.7) | 118.1 (41.7) | 10.5* (0.3) | 39.5 (2.7) | 4.68 (0.04) | 435 (295) | 23.3 (no) | 1.08 (no) | 3.35 (no) |

TABLE 1-continued

Partial readings on hematology and serum chemistry

| Dose (mg/kg) | ALT (U/L) | AST (U/L) | BUN (mmol/L) | TP (g/L) | WBC (×10$^9$ cells) | PLT (×10$^9$ cells) | NEUT (%) | #NEUT (×10$^9$ cells) | #LYMPH (×10$^9$ cells) |
|---|---|---|---|---|---|---|---|---|---|
| 100 | 33.2 (10.2) | 131.6 (27.8) | 7.3 (1.6) | 40.8 (3.3) | 10.77* (4.26) | 668 (202) | 46.6 (no) | 3.62 (no) | 3.5 (no) |
| 500 | 74.5* (21.6) | 151.2 (37.1) | 9.1 (0.3) | 49.5* (1.5) | 8.38 (1.32) | 1075 (99) | 40.5 (3.4) | 3.4 (0.64) | 4.81 (0.81) |

Table 1 displays partial readings on hematology and serum chemistry, wherein the listed are group means with SD (standard deviation) inside the parentheses, and wherein the * depicts a statistical significance ($p < 0.05$), and wherein the "no" means a standard deviation is not available due to sample size, and wherein ALT means alanine aminotransferase, AST aspartate aminotransferase, TP total protein, BUN blood urea nitrogen, WBC white blood cell count, PLT platelet, NEUT neutrophils, #NEUT number of neutrophils, and #LYMPH number of lymphocytes.

Example 5

Materials

Female BALB/c nude mice were supplied by Shanghai SLAC Laboratory Animals, Co. Ltd. (Shanghai, China). Female ICR mice were purchased from Shanghai Sippr-BK Laboratory Animal Co. Ltd. (Shanghai, China). Female 615 mice were from Institute of Hematology, Chinese Academy of Medical Sciences (Tianjin, China). Mice of 6 to 8 weeks of age were individually marked and coded. The animals were kept in laminar flow rooms at a constant temperature of 20 to 25° C. and humidity of 40 to 70%. The bedding material was corn cob, which was changed twice weekly. Animals had free access to sterile dry granule food and sterile drinking water during the entire procedure of studies.

Cell lines HCT116 (human colon cancer), M14 (human skin cancer), A375 (human skin cancer), SGC7901 (human stomach cancer), Ketr-3 (human kidney cancer), S180 (mouse soft tissue cancer/sarcoma), and U14 (mouse cervical cancer) were purchased from Chinese Academy of Medical Sciences & Peking Union Medical College (Beijing, China). Cell lines SW116 (human colon cancer), Siha (human cervical cancer), T24 (Human bladder cancer), CFPAC-1 (human pancreatic cancer), and MFC (mouse stomach cancer) were from Cell Center, Shanghai Academy of Life Sciences, Chinese Academy of Sciences (Shanghai, China).

ITE was customer manufactured by Shanghai ChemPartner Co., Ltd. (Shanghai, China) for AhR Pharmaceuticals, Inc. (Madison, Wis., USA). The lot number of the compound in AhR Pharmaceuticals' system is AHR-003. DMSO was supplied by Sigma-Aldrich (St. Louis, Mo., USA). Water used was the triple distilled water.

Methods

All the procedures related to animal handling, care, and the treatment in the study were performed following guidelines of KeyGen Biotechn Co., Ltd. (Nanjing, China), a contract research organization we hired, based on the guidance of the Association for Assessment and Accreditation of Laboratory Animal Care (AAALAC). Animals were checked for any effects of tumor growth and drug treatment on normal behavior such as mobility, food and water consumption, body weight gain/loss (bodyweights were measured every two days), eye/hair matting, and any other abnormal effect. Death and observed clinical signs were recorded. Individual animals with a tumor volume exceeding 3,000 mm$^3$ or animals of a group with a mean tumor volume exceeding 2,000 mm$^3$ were euthanized. In addition, animals showing signs of severe distress and/or pain or losing the capability of accessing adequate food or water were humanely sacrificed.

Oral injection of water was initiated at the same day i.p. administration of ITE was started. Daily oral gavage at 10 or 20 ml/kg was performed immediately following daily i.p. injection of ITE or DMSO continuously for the entire duration of the study. Both oral and i.p. injection were accidentally skipped at day 14 due to a mistake of the experimenter(s) and all of the other dosing were executed normally. Bodyweights (individual), food consumed (in group), feces weights (in group), and feces appearance (in group) were recorded every two days. Death of animal(s) and approximate cause of death etc. were also recorded.

Cell lines HCT116, Siha, MFC were cultured in DMEM medium (high glucose) supplemented with 10% fetal bovine serum (FBS), SW116 and T24 in RPMI-1640 medium with 10% FBS, M14 and A375 in DMEM medium (high glucose) with 10% calf serum (CS), SGC7901 and Ketr-3 in RPMI-1640 medium with 10% CS, and CFPAC-1 in IMDM medium with 10% FBS. All of the cells were cultured, in the presence of 100 U/ml penicillin and 100 µg/ml streptomycin, at 37° C. in an atmosphere of 5% $CO_2$ in air. The tumor cells were routinely subcultured twice a week. The cells growing in an exponential phase were harvested and counted for tumor inoculation. Cell lines 5180 and U14 were maintained in ascites (peritoneal cavity fluid) of mice and were harvested and counted for tumor inoculation.

Each mouse was inoculated subcutaneously in right armpit with about 1×10$^6$ cells in 0.1 ml of PBS for tumor development. While cells of human in origin were inoculated into female BALB/c nude mice, MFC cells were inoculated into female 615 mice and U14 and 5180 cells into female ICR mice. When a mean tumor volume reached 50 to 150 mm$^3$ as indicated, the tumor-bearing mice were divided randomly into vehicle control and ITE treatment group. Each group was consisted of 5 tumor-bearing mice. Vehicle (DMSO) or ITE in the vehicle at specified doses were administered to the mice by i.p. (intraperitoneal) injection at a volume of 2 ml/kg once daily for 28 continuous days or less for those reaching set tumor volumes earlier. A dose of 100-200 mg/kg designates a regimen of 100 mg/kg administered at the first 10 days and 200 mg/kg rest of days. Similarly, a dose of 200-300 mg/kg represents a scheme of 200 mg/kg dosed at the first 6 days and 300 mg/kg rest of days. Following each i.p. injection of ITE or vehicle alone, an oral gavage of 20 ml/kg water was performed to each mouse.

Tumor volume was measured every two days in two dimensions using a caliper and the volume was calculated with a formula of: $V=0.5\ a\times b^2$, where a and b are the long and short diameter (in mm) of a tumor, respectively. The tumor volume was then used for calculations of both TGI (Tumor Growth Inhibition) and TGD (Tumor Growth Delay). The TGI was determined by: $TGI=(1-\Delta T/\Delta C)\times 100\%$, where $\Delta T$ was a difference between the mean tumor volume at a specified day of observation and that at the day treatment starts (day 0) for a drug treated group whereas $\Delta C$ was the same difference measured for the control group. The TGD was calculated as: $TGD=T-C$, where T was the time (in days) required for tumors in a drug treated group to reach a predetermined mean tumor volume and C the time (in days) in the control group to reach the same volume.

Summary statistics, including mean and the standard error of the mean (SEM), were provided for the tumor volume of each group at each time point. Statistical analysis (Student's t-Test) of difference in tumor volumes between vehicle control and ITE treatment group was conducted by Excel 2010 at each time point and $P<0.05$ was considered to be statistically significant.

Results

Mice administered with ITE at either low (200 mg/kg) or high (300 mg/kg) level showed "dry" feces visually after one week of dosing (Table 2). In day 28 of ITE treatment, feces of oral water treated mice became "moderate" from "dry" and kept the appearance while ITE treated mice without oral water dosing kept their feces in "dry" appearance. While most of the mice survived the entire experimental procedure for a total of 40 days, one ITE low dose (200 mg/kg) and one ITE high dose (300 mg/kg) treated mice without oral water administration did die at day 28 and 36, respectively, illustrating the potential benefit of the oral water regimen (in addition to free access to drinking water) in ITE dosed mice (Table 2). Oral gavage of 20 ml/kg water following ITE or vehicle dosing becomes a standard protective procedure in studies reported in the present invention.

Figure 4A:
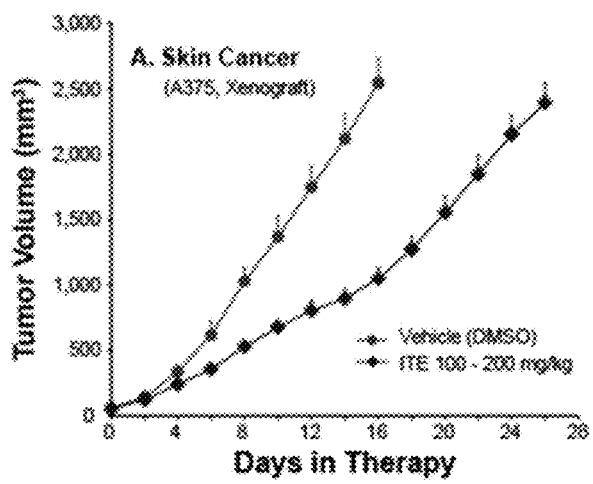
FIGS. 4A-4F are graphs illustrating the growth inhibition (mean+SEM, n=5) of cancer tissues derived from human and mouse cancer cells in response to ITE administration (i.p. injection, DMSO as vehicle, once daily continuous) at doses of 100-200 mg/kg (100 mg/kg first 10 days and 200 mg/kg then) or 200-300 mg/kg (200 mg/kg first 6 days and 300 mg/kg then) as indicated.
Figure 4B:
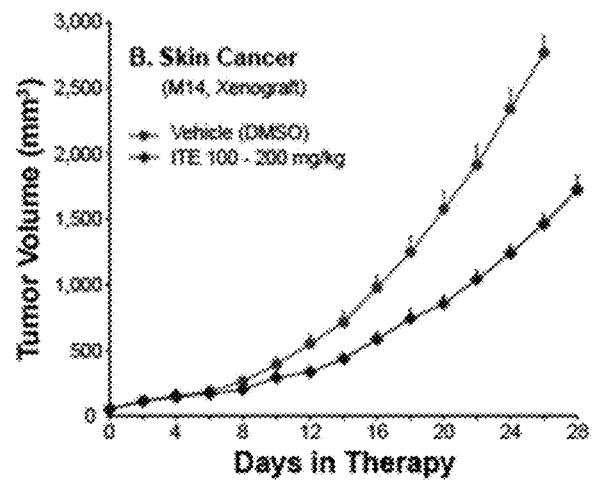
Figure 4C:
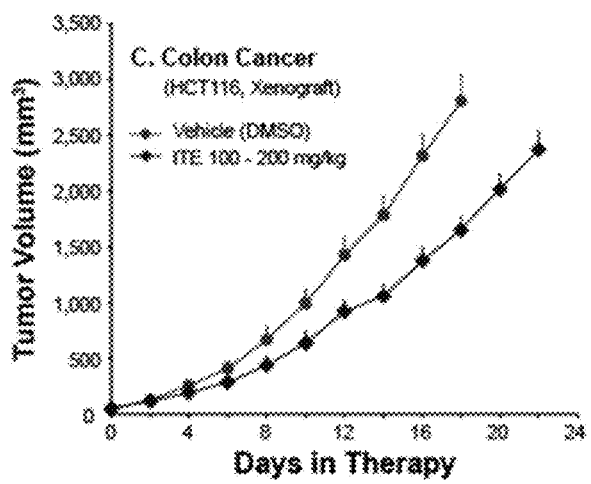
Figure 4D:
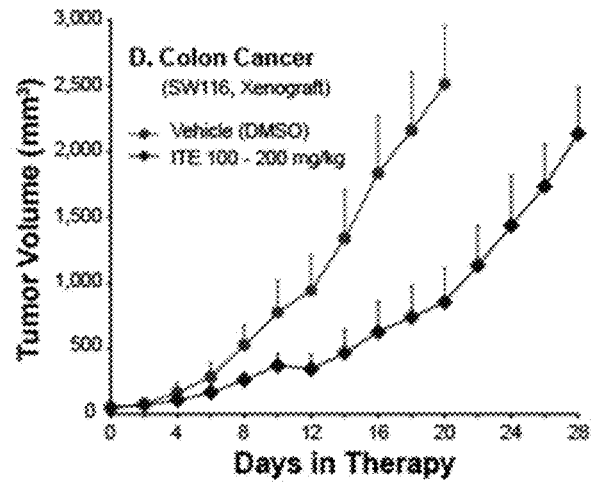
Figure 4E:
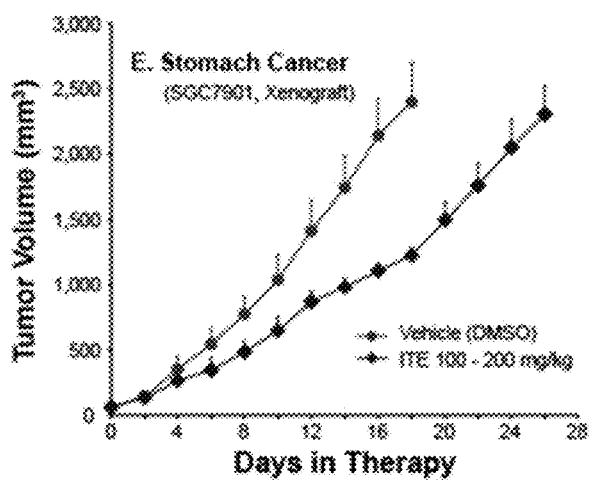
Figure 4F:
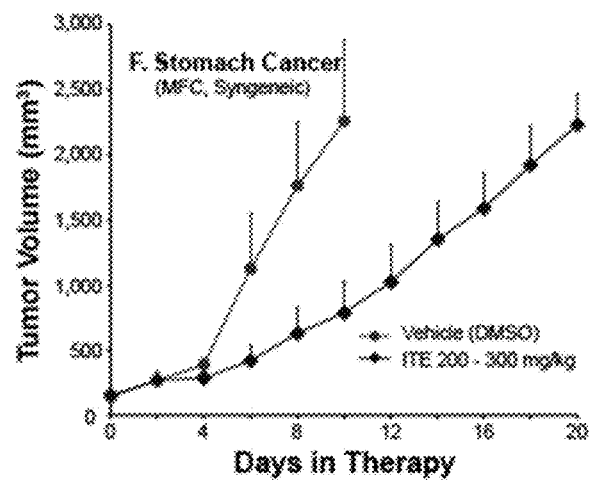

ITE demonstrated significant anticancer capability on human skin cancer xenograft model (cell line A375, FIG. 4A; cell line M14, FIG. 4B; 100-200 mg/kg), human colon cancer xenograft model (cell line HCT116, FIG. 4C; cell line SW116, FIG. 4D; 100-200 mg/kg), human stomach cancer xenograft model (cell line SGC7801, FIG. 4E; 100-200 mg/kg), mouse stomach cancer homograft (syngeneic) model (cell line MFC, FIG. 4F; 200-300 mg/kg), human pancreatic cancer xenograft model (cell line CFPAC-1, FIG. 5A; 100-200 mg/kg), human kidney cancer xenograft model (cell line Ketr-3, FIG. 5B; 100-200 mg/kg), human bladder cancer xenograft model (cell line T24, FIG. 5C; 100-200 mg/kg), mouse soft tissue cancer/sarcoma homograft (syngeneic) model (cell line S180, FIG. 5D; 200 mg/kg), human cervical cancer xenograft model (cell line Siha, FIG. 5E; 100-200 mg/kg), and mouse cervical cancer homograft (syngeneic) model (cell line U14, FIG. 5F; 200 mg/kg).

Table 2 illustrates effects of p.o. water administration (oral gavage) on i.p. ITE dosed mice, wherein "ITE-0", "ITE-L", and "ITE-H" represent, respectively, no ITE, low ITE (200 mg/kg), and high ITE (300 mg/kg) treatment; and wherein "Water-0", "Water-L", and "Water-H" indicate, respectively, no water, low water (10 ml/kg), and high water (20 ml/kg) administration; and wherein "M" and "D" stands for "Moderate" and "Dry", respectively, in visual inspection of feces appearance; and wherein the numbers follow either "M" or "D" represent number(s) of mice that died during experimentation.

TABLE 2

Effects of Oral Water Administration on ITE Dosed Mice

| Days | ITE-0 + Water-0 | ITE-L + Water-0 | ITE-L + Water-L | ITE-L + Water-H | ITE-H + Water-0 | ITE-H + Water-L | ITE-H + Water-H |
|---|---|---|---|---|---|---|---|
| 0  | M, 0 | M, 0 | M, 0 | M, 0 | M, 0 | M, 0 | M, 0 |
| 2  | M, 0 | M, 0 | M, 0 | M, 0 | M, 0 | M, 0 | M, 0 |
| 4  | M, 0 | M, 0 | M, 0 | M, 0 | M, 0 | M, 0 | M, 0 |
| 6  | M, 0 | M, 0 | M, 0 | M, 0 | M, 0 | M, 0 | M, 0 |
| 8  | M, 0 | D, 0 | D, 0 | D, 0 | D, 0 | D, 0 | D, 0 |
| 10 | M, 0 | D, 0 | D, 0 | D, 0 | D, 0 | D, 0 | D, 0 |
| 12 | M, 0 | D, 0 | D, 0 | D, 0 | D, 0 | D, 0 | D, 0 |
| 14 | M, 0 | D, 0 | D, 0 | D, 0 | D, 0 | D, 0 | D, 0 |
| 18 | M, 0 | D, 0 | D, 0 | D, 0 | D, 0 | D, 0 | D, 0 |
| 18 | M, 0 | D, 0 | D, 0 | D, 0 | D, 0 | D, 0 | D, 0 |
| 20 | M, 0 | D, 0 | D, 0 | D, 0 | D, 0 | D, 0 | D, 0 |
| 22 | M, 0 | D, 0 | D, 0 | D, 0 | D, 0 | D, 0 | D, 0 |
| 24 | M, 0 | D, 0 | D, 0 | D, 0 | D, 0 | D, 0 | D, 0 |
| 26 | M, 0 | D, 0 | D, 0 | D, 0 | D, 0 | D, 0 | D, 0 |
| 28 | M, 0 | D, 1 | M, 0 | M, 0 | D, 0 | M, 0 | M, 0 |
| 30 | M, 0 | D, 1 | M, 0 | M, 0 | D, 0 | M, 0 | M, 0 |
| 32 | M, 0 | D, 1 | M, 0 | M, 0 | D, 0 | M, 0 | M, 0 |
| 34 | M, 0 | D, 1 | M, 0 | M, 0 | D, 0 | M, 0 | M, 0 |
| 36 | M, 0 | D, 1 | M, 0 | M, 0 | D, 1 | M, 0 | M, 0 |
| 38 | M, 0 | D, 1 | M, 0 | M, 0 | D, 1 | M, 0 | M, 0 |
| 40 | M, 0 | D, 1 | M, 0 | M, 0 | D, 1 | M, 0 | M, 0 |

TGI's (Tumor Growth Inhibition), P values of Student's t-Test for the difference between vehicle and ITE treatment group in tumor volume calculated at the days TGI's were calculated, TGD's (Tumor Growth Delay), and percentages of bodyweight loss at the end of therapies (relative to the weights at the beginning) were listed in Table 3. There was no single animal death in either vehicle or ITE treatment group in any model in the entire therapies.

Table 3 lists several calculated numbers that help to further dissect the information from mouse cancer model studies, wherein "TGI (%)" means percentage of tumor growth inhibition as defined in the section of Methods, and wherein "TGI at day" represents the day at which the TGI was calculated, and wherein "P at TGI day" denotes the P value of the Student's t-Test for the difference between vehicle and ITE treatment group in tumor volume calculated at the day TGI was calculated, and wherein "TGD" indicates tumor growth delay in days as described in the section of Methods, and wherein "TGD at Vol." stands for tumor volume at which the TGD was calculated, and wherein "Weight Loss" designates percentage of bodyweight loss at the end of the therapy relative to the weight at the beginning of the therapy.

TABLE 3

Mouse Cancer Model Studies

| Cell Line | Cancer | TGI (%) | TGI at day | P at TGI day | TGD | TGD at Vol. | Weight Loss |
|---|---|---|---|---|---|---|---|
| A375 | Skin | 60 | 16 | $1 \times 10^{-4}$ | 7 | 1,000 | 18 |
| M14 | Skin | 48 | 26 | $1 \times 10^{-4}$ | 5 | 1,000 | 15 |
| HCT116 | Colon | 41 | 18 | $2 \times 10^{-3}$ | 3 | 1,000 | 9 |
| SW116 | Colon | 67 | 20 | $1 \times 10^{-4}$ | 9 | 1,000 | 15 |
| SGC7901 | Stomach | 50 | 18 | $3 \times 10^{-5}$ | 4 | 1,000 | 12 |
| MFC | Stomach | 70 | 10 | $1.1 \times 10^{-3}$ | 9 | 2,000 | 16 |
| CFPAC-1 | Pancreas | 58 | 26 | $1 \times 10^{-4}$ | 8 | 1,000 | 14 |
| Ketr-3 | Kidney | 74 | 28 | $2 \times 10^{-7}$ | 9 | 500 | 13 |
| T24 | Bladder | 66 | 26 | $5 \times 10^{-6}$ | 9 | 1,000 | 13 |
| S180 | Soft Tissue | 33 | 8 | $2 \times 10^{-3}$ | 1.5 | 2,000 | 9 |
| Siha | Cervix | 53 | 24 | $5 \times 10^{-7}$ | 7 | 1,000 | 19 |
| U14 | Cervix | 46 | 6 | $3 \times 10^{-2}$ | 3 | 2,000 | 4 |

The present invention can be applied to the area of cancer intervention or eradication for human beings and other animals, especially mammals.

It will be understood that various details of the presently disclosed subject matter can be changed without departing from the scope of the subject matter disclosed herein. Furthermore, the foregoing description is for the purpose of illustration only, and not for the purpose of limitation.

Throughout this document, various references are mentioned. All such references are incorporated herein by reference, including the references set forth in the following list:

REFERENCES

1. Poland A, Knutson J C. 2,3,7,8-tetrachlorodibenzo-p-dioxin and related halogenated aromatic hydrocarbons: examination of the mechanism of toxicity. *Annu Rev Pharmacol Toxicol.* 1982; 22:517-554. doi:10.1146/annurev.pa.22.040182.002505.
2. Poellinger L. Mechanistic aspects—the dioxin (aryl hydrocarbon) receptor. *Food Addit Contam.* 2000; 17(4):261-6.
3. Bock K W, Köhle C. Ah receptor- and TCDD-mediated liver tumor promotion: clonal selection and expansion of cells evading growth arrest and apoptosis. *Biochem Pharmacol.* 2005; 69(10):1403-1408. doi:10.1016/j.bcp.2005.02.004.
4. Stevens E A, Mezrich J D, Bradfield C A. The aryl hydrocarbon receptor: a perspective on potential roles in the immune system. *Immunology.* 2009; 127(3):299-311. doi:10.1111/j.1365-2567.2009.03054.x.
5. Puga A, Tomlinson C R, Xia Y. Ah receptor signals cross-talk with multiple developmental pathways. *Biochem Pharmacol.* 2005; 69(2):199-207. doi:10.1016/j.bcp.2004.06.043.
6. Safe S, McDougal A. Mechanism of action and development of selective aryl hydrocarbon receptor modulators for treatment of hormone-dependent cancers (Review). *Int J Oncol.* 2002; 20(6):1123-8.
7. DeLuca H F, Clagett-Dame M, Song J, Helfand S, Akhtar N. U.S. Pat. No. 7,419,992—Use of aryl hydrocarbon receptor ligand as a therapeutic intervention in angiogenesis-implicated disorders. 2008. Available at: http://patft.uspto.gov/netacgi/nph-Parser?Sect1=PTO2&Sect2=HITOFF&p=1&u=%2Fnetahtml%2FPTO%2Fsearch-bool.html&r=8&f=G&l=50&col=AND&d=PTXT&s1=Jiasheng.INNM.&OS=IN/Jiasheng&RS=IN/Jiasheng. Accessed Jul. 19, 2013.
8. Dietrich C, Kaina B. The aryl hydrocarbon receptor (AhR) in the regulation of cell-cell contact and tumor growth. *Carcinogenesis.* 2010; 31(8):1319-1328. doi:10.1093/carcin/bgq028.
9. Song J, Clagett-Dame M, Peterson R E, et al. A ligand for the aryl hydrocarbon receptor isolated from lung. *Proc Natl Acad Sci USA.* 2002; 99(23):14694-9. doi:10.1073/pnas.232562899.
10. DeLuca H F, Song J, Clagett-Dame M, et al. U.S. Pat. No. 6,916,834—Preparations and use of an Ah receptor ligand, 2-(1'H-indole-3'-carbonyl)-thiazole-4-carboxylic acid methyl ester. 2005. Available at: http://patft.uspto.gov/netacgi/nph-Parser?Sect1=PTO2&Sect2=HITOFF&p=1&u=%2Fnetahtml%2FPTO%2Fsearch-bool.html&r=10&f=G&l=50&col=AND&d=PTXT&s1=Jiasheng.INNM.&OS=IN/Jiasheng&RS=IN/Jiasheng. Accessed Jul. 19, 2013.
11. Fritz W A, Lin T-M, Safe S, Moore R W, Peterson R E. The selective aryl hydrocarbon receptor modulator 6-methyl-1,3,8-trichlorodibenzofuran inhibits prostate tumor metastasis in TRAMP mice. *Biochem Pharmacol.* 2009; 77(7):1151-1160. doi:10.1016/j.bcp.2008.12.015.
12. McDougal A, Wilson C, Safe S. Inhibition of 7,12-dimethylbenz[a]anthracene-induced rat mammary tumor growth by aryl hydrocarbon receptor agonists. *Cancer Lett.* 1997; 120(1):53-63.
13. Holcomb M, Safe S. Inhibition of 7,12-dimethylbenzanthracene-induced rat mammary tumor growth by 2,3,7,8-tetrachlorodibenzo-p-dioxin. *Cancer Lett.* 1994; 82(1):43-47.
14. McDougal A, Wormke M, Calvin J, Safe S. Tamoxifen-induced antitumorigenic/antiestrogenic action synergized by a selective aryl hydrocarbon receptor modulator. *Cancer Res.* 2001; 61(10):3902-3907.
15. Gierthy J F, Bennett J A, Bradley L M, Cutler D S. Correlation of in vitro and in vivo growth suppression of MCF-7 human breast cancer by 2,3,7,8-tetrachlorodibenzo-p-dioxin. *Cancer Res.* 1993; 53(13):3149-3153.
16. Zhang S, Lei P, Liu X, et al. The aryl hydrocarbon receptor as a target for estrogen receptor-negative breast cancer chemotherapy. *Endocr Relat Cancer.* 2009; 16(3):835-844. doi:10.1677/ERC-09-0054.
17. Kawajiri K, Kobayashi Y, Ohtake F, et al. Aryl hydrocarbon receptor suppresses intestinal carcinogenesis in ApcMin/+mice with natural ligands. *Proc Natl Acad Sci USA.* 2009; 106(32):13481-13486. doi:10.1073/pnas.0902132106.

18. O'Donnell E F, Kopparapu P R, Koch D C, et al. The aryl hydrocarbon receptor mediates leflunomide-induced growth inhibition of melanoma cells. *Plos One.* 2012; 7(7):e40926. doi:10.1371/journal.pone.0040926.
19. Simon T, Aylward L L, Kirman C R, Rowlands J C, Budinsky R A. Estimates of cancer potency of 2,3,7,8-tetrachlorodibenzo(p)dioxin using linear and nonlinear dose-response modeling and toxicokinetics. *Toxicol Sci Off J Soc Toxicol.* 2009; 112(2):490-506. doi:10.1093/toxsci/kfp232.
20. Ishida M, Mikami S, Kikuchi E, et al. Activation of the aryl hydrocarbon receptor pathway enhances cancer cell invasion by upregulating the MMP expression and is associated with poor prognosis in upper urinary tract urothelial cancer. *Carcinogenesis.* 2010; 31(2):287-295. doi:10.1093/carcin/bgp222.
21. Ray S, Swanson H I. Activation of the aryl hydrocarbon receptor by TCDD inhibits senescence: a tumor promoting event? *Biochem Pharmacol.* 2009; 77(4):681-688. doi:10.1016/j.bcp 0.2008.11.022.
22. Knerr S, Schrenk D. Carcinogenicity of 2,3,7,8-tetrachlorodibenzo-p-dioxin in experimental models. *Mol Nutr Food Res.* 2006; 50(10):897-907. doi:10.1002/mnfr.200600006.
23. Yu Z, Loehr C V, Fischer K A, et al. In utero exposure of mice to dibenzo[a,1]pyrene produces lymphoma in the offspring: role of the aryl hydrocarbon receptor. *Cancer Res.* 2006; 66(2):755-762. doi:10.1158/0008-5472.CAN-05-3390.
24. Song J. U.S. patent application Ser. No. 12/0214,853—ITE for Cancer Intervention and Eradication. A1. Available at: http://appft1.uspto.gov/netacgi/nph-Parser?Sect1=PTO2&Sect2=HITOFF&p=1&u=%2Fnetahtml%2FPTO%2Fsearch-bool.html&r=4&f=G&1=50&co1=AND&d=PG01&s1=Jiasheng.IN.&OS=IN/Jiasheng&RS=IN/Jiasheng. Accessed Jul. 19, 2013.
25. Quintana F J, Basso A S, Iglesias A H, et al. Control of T(reg) and T(H)17 cell differentiation by the aryl hydrocarbon receptor. *Nature.* 2008; 453(7191):65-71. doi:10.1038/nature06880.
26. Henry E C, Bemis J C, Henry O, Kende A S, Gasiewicz T A. A potential endogenous ligand for the aryl hydrocarbon receptor has potent agonist activity in vitro and in vivo. *Arch Biochem Biophys.* 2006; 450(1):67-77. doi:10.1016/j.abb.2006.02.008.
27. Brauze D, Widerak M, Cwykiel J, Szyfter K, Baer-Dubowska W. The effect of aryl hydrocarbon receptor ligands on the expression of AhR, AhRR, ARNT, Hiflalpha, CYP1A1 and NQO1 genes in rat liver. *Toxicol Lett.* 2006; 167(3):212-220. doi:10.1016/j.toxlet.2006.09.010.
28. Bermùdez de Leòn M, Gómez P, Elizondo G, Zatarain-Palacios R, García-Sierra F, Cisneros B. Beta-naphthoflavone represses dystrophin Dp71 expression in hepatic cells. *Biochim Biophys Acta.* 2006; 1759(3-4):152-158. doi: 10.1016/j.bbaexp.2006.03.005.
29. Okino S T, Pookot D, Basak S, Dahiya R. Toxic and chemopreventive ligands preferentially activate distinct aryl hydrocarbon receptor pathways: implications for cancer prevention. *Cancer Prev Res Phila Pa.* 2009; 2(3):251-256. doi:10.1158/1940-6207.CAPR-08-0146.
30. Morrow D, Qin C, Smith R, Safe S. Aryl hydrocarbon receptor-mediated inhibition of LNCaP prostate cancer cell growth and hormone-induced transactivation. *J Steroid Biochem Mol Biol.* 2004; 88(1):27-36. doi:10.1016/j.jsbmb.2003.10.005.
31. Sanderson J T, Slobbe L, Lansbergen G W, Safe S, van den Berg M. 2,3,7,8-Tetrachlorodibenzo-p-dioxin and diindolylmethanes differentially induce cytochrome P450 1A1, 1B1, and 19 in H295R human adrenocortical carcinoma cells. *Toxicol Sci Off J Soc Toxicol.* 2001; 61(1):40-48.
32. John A R, Bramhall S R, Eggo M C. Antiangiogenic therapy and surgical practice. *Br J Surg.* 2008; 95(3):281-293. doi:10.1002/bjs.6108.
33. Roukos D H, Tzakos A, Zografos G. Current concerns and challenges regarding tailored anti-angiogenic therapy in cancer. *Expert Rev Anticancer Ther.* 2009; 9(10):1413-1416. doi:10.1586/era.09.116.
34. English B C, Price D K, Figg W D. VEGF inhibition and metastasis: possible implications for antiangiogenic therapy. *Cancer Biol Ther.* 2009; 8(13):1214-1225.
35. Loges S, Mazzone M, Hohensinner P, Carmeliet P. Silencing or fueling metastasis with VEGF inhibitors: antiangiogenesis revisited. *Cancer Cell.* 2009; 15(3):167-170. doi:10.1016/j.ccr.2009.02.007.
36. Ebos J M L, Lee C R, Cruz-Munoz W, Bjarnason G A, Christensen J G, Kerbel R S. Accelerated metastasis after short-term treatment with a potent inhibitor of tumor angiogenesis. *Cancer Cell.* 2009; 15(3):232-239. doi:10.1016/j.ccr.2009.01.021.
37. Pàez-Ribes M, Allen E, Hudock J, et al. Antiangiogenic therapy elicits malignant progression of tumors to increased local invasion and distant metastasis. *Cancer Cell.* 2009; 15(3):220-231. doi:10.1016/j.ccr.2009.01.027.
38. Elizondo G, Fernandez-Salguero P, Sheikh M S, et al. Altered cell cycle control at the G(2)/M phases in aryl hydrocarbon receptor-null embryo fibroblast. *Mol Pharmacol.* 2000; 57(5):1056-63.
39. Puga A, Marlowe J, Barnes S, et al. Role of the aryl hydrocarbon receptor in cell cycle regulation. *Toxicology.* 2002; 181-182:171-7.
40. Marlowe J L, Knudsen E S, Schwemberger S, Puga A. The aryl hydrocarbon receptor displaces p300 from E2F-dependent promoters and represses S phase-specific gene expression. *J Biol Chem.* 2004; 279(28):29013-22. doi:10.1074/jbc.M404315200.
41. Kajta M, Wójtowicz A K, Maćkowiak M, Lasoń W. Aryl hydrocarbon receptor-mediated apoptosis of neuronal cells: a possible interaction with estrogen receptor signaling. *Neuroscience.* 2009; 158(2):811-822. doi:10.1016/j.neuroscience.2008.10.045.
42. Singh N P, Nagarkatti M, Nagarkatti P. Primary peripheral T cells become susceptible to 2,3,7,8-tetrachlorodibenzo-p-dioxin-mediated apoptosis in vitro upon activation and in the presence of dendritic cells. *Mol Pharmacol.* 2008; 73(6):1722-1735. doi:10.1124/mol.107.043406.
43. Park K-T, Mitchell K A, Huang G, Elferink C J. The aryl hydrocarbon receptor predisposes hepatocytes to Fas-mediated apoptosis. *Mol Pharmacol.* 2005; 67(3):612-22. doi:10.1124/mol.104.005223.
44. Jux B, Kadow S, Esser C. Langerhans cell maturation and contact hypersensitivity are impaired in aryl hydrocarbon receptor-null mice. *J Immunol Baltim Md 1950.* 2009; 182(11):6709-6717. doi:10.4049/jimmunol.0713344.
45. Sutter C H, Yin H, Li Y, et al. EGF receptor signaling blocks aryl hydrocarbon receptor-mediated transcription and cell differentiation in human epidermal keratinocytes. *Proc Natl Acad Sci USA.* 2009; 106(11):4266-4271. doi:10.1073/pnas.0900874106.
46. Hall J M, Barhoover M A, Kazmin D, McDonnell D P, Greenlee W F, Thomas R S. Activation of the Aryl-Hydrocarbon Receptor Inhibits Invasive and Metastatic Features of Human Breast Cancer Cells and Promotes Breast Cancer Cell Differentiation. *Mol Endocrinol Baltim Md.* 2009. doi:10.1210/me.2009-0346.

47. Oenga G N, Spink D C, Carpenter D O. TCDD and PCBs inhibit breast cancer cell proliferation in vitro. *Toxicol Vitro Int J Publ Assoc Bibra.* 2004; 18(6):811-9. doi:10.1016/j.tiv.2004.04.004.

48. Jana N R, Sarkar S, Ishizuka M, Yonemoto J, Tohyama C, Sone H. Cross-talk between 2,3,7,8-tetrachlorodibenzo-p-dioxin and testosterone signal transduction pathways in LNCaP prostate cancer cells. *Biochem Biophys Res Commun.* 1999; 256(3):462-8. doi:10.1006/bbrc.1999.0367.

49. Morrow D, Qin C, Smith R, Safe S. Aryl hydrocarbon receptor-mediated inhibition of LNCaP prostate cancer cell growth and hormone-induced transactivation. *J Steroid Biochem Mol Biol.* 2004; 88(1):27-36. doi:10.1016/j.jsbmb.2003.10.005.

50. Veldhoen M, Hirota K, Westendorf A M, et al. The aryl hydrocarbon receptor links TH17-cell-mediated autoimmunity to environmental toxins. *Nature.* 2008; 453(7191):106-109. doi:10.1038/nature06881.

51. Koliopanos A, Kleeff J, Xiao Y, et al. Increased arylhydrocarbon receptor expression offers a potential therapeutic target for pancreatic cancer. *Oncogene.* 2002; 21(39):6059-6070. doi:10.1038/sj.onc.1205633.

52. Kashani M, Steiner G, Haitel A, et al. Expression of the aryl hydrocarbon receptor (AhR) and the aryl hydrocarbon receptor nuclear translocator (ARNT) in fetal, benign hyperplastic, and malignant prostate. *Prostate.* 1998; 37(2):98-108.

53. Gluschnaider U, Hidas G, Cojocaru G, Yutkin V, Ben-Neriah Y, Pikarsky E. beta-TrCP inhibition reduces prostate cancer cell growth via upregulation of the aryl hydrocarbon receptor. *Plos One.* 2010; 5(2):e9060. doi:10.1371/journal.pone.0009060.

54. Peng T-L, Chen J, Mao W, et al. Potential therapeutic significance of increased expression of aryl hydrocarbon receptor in human gastric cancer. *World J Gastroenterol Wjg.* 2009; 15(14):1719-1729.

55. Liu Z, Wu X, Zhang F, et al. AhR expression is increased in hepatocellular carcinoma. *J Mol Histol.* 2013. doi:10.1007/s10735-013-9495-6.

56. Lin P, Chang H, Tsai W-T, et al. Overexpression of aryl hydrocarbon receptor in human lung carcinomas. *Toxicol Pathol.* 2003; 31(1):22-30.

57. Zhang J, Zong H, Li S, Zhang D, Zhang L, Xia Q. Activation of aryl hydrocarbon receptor suppresses invasion of esophageal squamous cell carcinoma cell lines. *Tumori.* 2012; 98(1):152-157. doi:10.1700/1053.11514.

The invention claimed is:

1. A method of stimulating the immune system in a human patient with cancer, comprising administering a therapeutically effective amount of 2-(1'H-indole-3'-carbonyl)-thiazole-4-carboxylic acid methyl ester (ITE) or a structural analog thereof to the patient, thereby treating the cancer, wherein the cancer is selected from a group consisting of skin, colorectal, stomach, pancreatic, kidney, bladder, soft tissue, and cervical cancer, and wherein said ITE has the formula:

Structural Formula 1

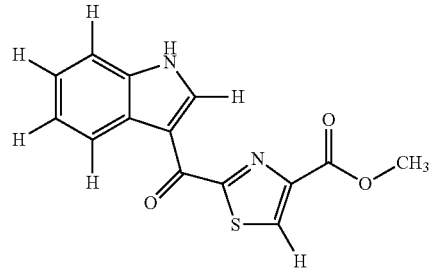

and wherein the ITE structural analog has the formula:

Structural Formula 4

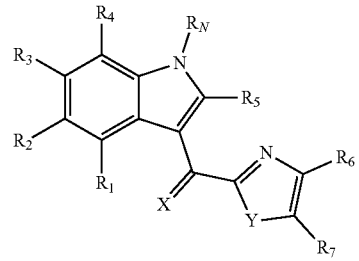

wherein
X is O (oxygen);
Y is O (oxygen) or S (sulfur);
$R_N$ is hydrogen or a nitrogen protective group;
$R_1$, $R_2$, $R_3$, $R_4$, and $R_5$ are independently selected from hydrogen, halo, hydroxy (—OH), thiol (—SH), cyano (—CN), alkyl, haloalkyl, amino, nitro (—NO$_2$), alkoxy, haloalkoxy, thioalkoxy; and
$R_6$ and $R_7$ are independently selected from hydrogen, halo, hydroxy, thiol, cyano, formyl, alkyl, haloalkyl, alkenyl, alkynyl, amino, nitro, alkoxy, haloalkoxy, thioalkoxy;

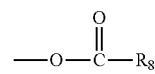

wherein $R_8$ is selected from hydrogen, halo, cyano, alkyl, haloalkyl, alkenyl, or alkynyl;

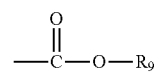

wherein $R_9$ is selected from hydrogen, halo, alkyl, haloalkyl, alkenyl, or alkynyl;

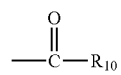

wherein $R_{10}$ is selected from hydrogen, halo, hydroxy, thiol, cyano, alkyl, haloalkyl, alkenyl, alkynyl, amino, or nitro; or

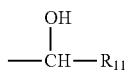

wherein $R_{11}$ is selected from hydrogen, halo, alkyl, haloalkyl, alkenyl, or alkynyl.

2. The method of claim 1, wherein the ITE structure analog has the following formula:

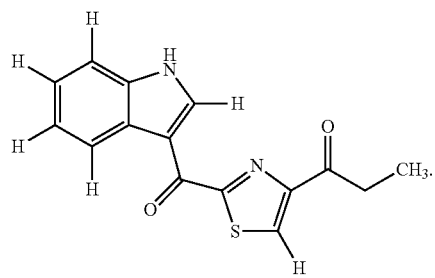

Structural Formula 2

3. The method of claim 1, wherein the ITE structure analog has the following formula:

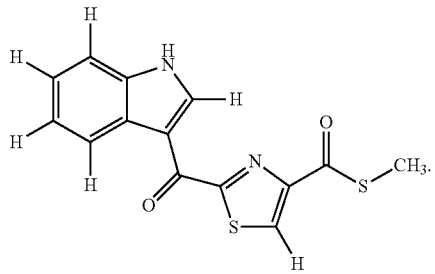

Structural Formula 3

4. The method of claim 1, wherein the patient has an increased count of cells selected from the group consisting of white blood cells, neutrophils, lymphocytes, and platelets after the administering step.

5. The method of claim 1, further comprising administering to the patient another cancer therapeutic agent.

6. The method of claim 1, wherein the ITE or structural analog thereof is combined with one or more pharmaceutically acceptable carriers to assist its administration to the patient.

7. The method of claim 1, wherein the ITE or structural analog thereof is administered by topical, enteral, or parenteral application.

8. The method of claim 1, further comprising administering a dose of water to the patient to reduce feces hardening caused by the ITE or structural analog thereof.

9. The method of claim 1, further comprising administering to the patient one or more other cancer therapeutic agents.

10. The method of claim 1, wherein a maintenance dosing of the ITE or structural analog thereof is provided after the subject is free of cancer to ensure cancer eradication.

* * * * *